US008080680B2

(12) United States Patent
Debonte et al.

(10) Patent No.: US 8,080,680 B2
(45) Date of Patent: Dec. 20, 2011

(54) CANOLA OIL FROM HYBRID *BRASSICA* VARIETIES

(75) Inventors: Lorin R. Debonte, Ft. Collins, CO (US); Xinmin Deng, Alberta (CA); Wade Stock, Manitoba (CA)

(73) Assignee: Cargill, Incorporateed, Wayzata, MN (US)

( * ) Notice: Subject to any disclaimer, the term of this patent is extended or adjusted under 35 U.S.C. 154(b) by 689 days.

(21) Appl. No.: 11/575,477

(22) PCT Filed: Sep. 16, 2005

(86) PCT No.: PCT/US2005/033215
§ 371 (c)(1),
(2), (4) Date: Apr. 21, 2008

(87) PCT Pub. No.: WO2006/034059
PCT Pub. Date: Mar. 30, 2006

(65) Prior Publication Data
US 2008/0199587 A1 Aug. 21, 2008

Related U.S. Application Data

(60) Provisional application No. 60/610,406, filed on Sep. 16, 2004.

(51) Int. Cl.
*A23D 9/00* (2006.01)
(52) U.S. Cl. ........................ 554/227; 426/601
(58) Field of Classification Search .................. 554/227; 426/601
See application file for complete search history.

(56) References Cited

U.S. PATENT DOCUMENTS

| 5,859,350 A | 1/1999 | DeBonte et al. |
| 6,051,539 A * | 4/2000 | Kodali et al. ................ 508/491 |
| 6,552,250 B1 | 4/2003 | Nykiforuk et al. |

FOREIGN PATENT DOCUMENTS

| EP | 1 329 154 | 7/2003 |
| EP | 1329154 A2 * | 7/2003 |
| WO | WO 97/21340 | 6/1997 |
| WO | WO 9721340 A1 * | 6/1997 |
| WO | WO 97/43907 | 11/1997 |
| WO | WO 9743907 A1 * | 11/1997 |
| WO | WO 2006/034059 | 3/2006 |

OTHER PUBLICATIONS

Neff, W. E. et al:. Oxidative stabilily of purified canola oil triacylglycerols with altered fatty acid compositions as affected by triacylglycerol composition and structure. Journal of the American Oil Chemists; Society, 71 (10), 1101-9 1994.*

Akoh and Moussata, "Characterization and Oxidative Stability of Enzymatically Produced Fish and Canola Oil-Based Structured Lipids," *JAOCS*, 2001, 78(1):25-30.

Beare-Rogers, "Dietary Fatty Acids in an Era of Genetic Modification," *Forum of Nutrition*, 2003, 56:63-64.

Bell et al., "The new dietary fats in health and disease," *J. Am. Dietetic Assoc.*, 1997, 97(3):280-286.

Billek, "Health aspects of thermoxidized oils and fats," *Eur. J. Lipid Sci. Technol.*, 2000, 102:587-593.

(Continued)

*Primary Examiner* — Deborah D Carr

(57) ABSTRACT

Canola oils from hybrid *Brassica* varieties and methods for producing hybrid *Brassica* varieties are described. The hybrid seeds have a low, mid, or high oleic acid content and a low linolenic acid content.

26 Claims, 3 Drawing Sheets

OTHER PUBLICATIONS

Cater, "Historical and scientific basis for the development of plant stanol ester foods as cholesterol-lowering agents," *Eur. Heart J. Suppl.*, 1999, S36-S44.

Clark, "Tocopherols and sterols from soybeans," *Lipid Technology*, 1996, 4 pages.

Daguet, "Phytosterols: highly promising compounds," *Lipid Technology*, 2000, 77-80.

El-Adawy and Taha, "Characteristics and composition of different seed oils and flours," *Food Chemistry*, 2001, 74(1):47-54.

El-Adawy and Taha, "Characteristics and Composition of Watermelon, Pumpkin, and Paprika Seed Oils and Flours," *J. Agric. Food Chem.*, 2001, 49(3):1253-1259.

Frankel et al., "Autoxidation of Polyunsaturated Triacylglycerols. II. Trilinolenoylglycerol," *Lipids*, 1990, 25(1):40-47.

Kubow, "The influence of positional distribution of fatty acids in native, interesterified and structure-specific lipids on lipoprotein metabolism and atherogenesis," *Nutritional Biochem.*, 1996, 7:530-541.

Lampert, "High-Stability Oils: What Are They? How Are They Made? Why Do We Need Them?" Chapter 15, 238-246, 1999.

Lau et al., "Effect of Randomization of the Oxidation of Corn Oil," *JAOCS*, 1982, 59(10):407-411.

Martin et al., "Effect of Fatty Acid Positional Distribution and Triacylglycerol Composition on Lipid By-Products Formation During Heat Treatment: III-Cyclic Fatty Acid Monomers Study," *JAOCS*, 1998, 75(12):1691-1697.

McDonald and Fitzpatrick, "Designer Vegetable Oils" Chapter 8, pp. 265-291, 2005.

Miyashita et al., "Autoxidation of Polyunsaturated Triacylglycerols. III. Synthetic Triacylglycerols Containing Linoleate and Linolenate," *Lipids*, 1990, 25(1):48-53.

"Modification of triglycerides by lipases: process technology and its application to the production of nutritionally improved fats," *Inform*, 1993, 4(5):580-585.

Neff and El-Agaimy, "Effect of Linoleic Acid Position in Triacylglycerols on their Oxidative Stability," *Lebensm.-Wiss. U.-Technol.*, 1996, 29:772-775.

Neff et al., "Effect of Triacylglycerol Composition and Structures on Oxidative Stability of Oils from Selected Soybean Germplasm," *JAOCS*, 1992, 69(2):111-118.

Neff et al., "Oxidative Stability as Affected by Triacylglycerol Composition and Structure of Purified Canola Oil Triacylglycerols from Genetically Modified Normal and High Stearic and Lauric Acid Canola Varieties," *Food Sci. Technol.*, 1997, 30(8):793-799.

Neff et al., "Oxidative Stability of Blends and Interesterified Blends of Soybean Oil and Palm Olein," *JAOCS*, 1994, 71:1111-1116.

Neff and List, "Oxidative Stability of Natural and Randomized High-Palmitic- and High-Stearic-Acid Oils from Genetically Modified Soybean Varieties," *JAOCS*, 1999, 78(7):825-831.

Neff et al., "Oxidative Stability of Purified Canola Oil Triacyglycerols with Altered Fatty Acid Compositions as Affected by Triacyglycerol Composition and Structure," *JAOCS*, 1994, 71:1101-1109.

Neff et al., "Photooxidation of Soybean Oils as Affected by Triacylglycerol Composition and Structure," *JAOCS*, 1993, 70(2):163-168.

Nielsen et al., "Oxidative Stability During Storage of Structured Lipids Produced from Fish Oil and Caprylic Acid," *JAOCS*, 2004, 81(4):375-384.

Raghuveer and Hammond, "The Influence of Glyceride Structure on the Rate of Autoxidation," *JAOCS*, 1967, 44:239-243.

Rousseau and Marangoni, "On Deciphering the Fat Structure-Functionality Mystery: The Case of Butter Fat," Physical Properties of Fats, Oils, and Emulsifiers, 1999, *JAOCS*, Champaign, IL, 112-128.

Sakurai and Pokorny, "The development and application of novel vegetable oils tailor-made for specific human dietary needs," *Eur. J. Lipid Sci. Technol.*, 2003, 105(12):769-778.

Shibasaki-Kitakawa et al., "Oxidation Kinetics of $\beta$-Carotene in Oleic Acid Solvent with Addition of an Antioxidant, $\alpha$-Tocopherol," *JAOCS*, 2004, 81(4):389-394.

Stanley, "Dietary triacylglycerol structure affects atherosclerosis and thrombosis," *Lipid Technol.*, 2003, 15(4):85-87.

Sugano et al., "Health Benefits of Rice Bran Oil," *Anticancer Res.*, 1999, 19:3651-3658.

Sum et al., "Predictive Molecular Model for the Thermodynamic and Transport Properties of Triacylglycerols," *J. Physical Chem. B*, 2003, 107(51):14443-14451.

Terao, "Factors Affecting the Oxidative Stability of Emulsified Oil and Membranous Phospholipids," *J. Oleo Sci.*, 2001, 50:393-397.

Wada and Koizumi, "Influence of the Position of Unsaturated Fatty Acid Esterified Glycerol on the Oxidation Rate of Triglyceride," *JAOCS*, 1983, 60:1105-1109.

Warner et al., "Flavor and Oxidative Stability of Soybean, Sunflower and Low Erucic Acid Rapeseed Oils," *JAOCS*, 1989, 66:558-564.

Webb et al., "A 91-Day Feeding Study in Rats with Caprenin," *Fd Chem. Toxic.*, 1993, 31:935-946.

Yli-Jokipii et al., "Effects of palm oil and transesterified palm oil on chylomicron and VLDL triacylglycerol structures and postprandial lipid response," *J. Lipid Res.*, 2001, 42(10):1618-1625.

* cited by examiner

CANOLA OIL FROM HYBRID *BRASSICA* VARIETIES

CROSS-REFERENCE TO RELATED APPLICATIONS

This application is a National Stage application under 35 U.S.C. §371 and claims benefit under 35 U.S.C. §119(a) of International Application No. PCT/US2005/033215 having an International Filing Date of Sep. 16, 2005, which claims the benefit of priority of U.S. Provisional Application No. 60/610,406 having a filing date of Sep. 16, 2004.

TECHNICAL FIELD

This invention relates to hybrid *Brassica* plants, and more particularly to hybrid *Brassica* plants yielding seeds having a low, mid, or high oleic acid content in combination with a low linolenic acid content, and the canola oil obtained from such plants.

BACKGROUND

Trans unsaturated fatty acids, or trans fats, are solid fats produced by partially hydrogenating liquid vegetable oils. Partially hydrogenated oils are used to prepare many food products. For example, partially hydrogenated oils typically are used to cook french fries and other fast foods. Many commercial baked goods also are prepared with partially hydrogenated oils to protect against spoilage. Dietary consumption of foods high in trans fats has been linked to increased serum cholesterol content. Thus, there is a need for food products that contain no or low levels of trans fats.

SUMMARY

The invention is based on the discovery that hybrid *Brassica* varieties can be produced that yield seeds having a fatty acid content tailored to the desired end use of the canola oil, e.g., a frying oil or an industrial oil. The triacylglycerol (TAG) composition and/or TAG structure of oils produced by hybrid *Brassica* varieties can be altered relative to that from a canola oil having a similar fatty acid content, but obtained from a non-hybrid *Brassica* variety. As such, canola oils obtained from hybrid *Brassica* varieties can have improved properties, including increased oxidative stability, flavor stability, and/or color stability.

In one aspect, the invention features a method for producing a hybrid *Brassica* plant. The method includes hybridizing one or more first *Brassica* plants having decreased delta-15 desaturase activity and one or more second *Brassica* plants having decreased delta-15 desaturase activity, wherein the first *Brassica* plants produce seeds yielding an oil having an oleic acid content of about 60% to about 74% and an α-linolenic acid content of about 0.8% to about 4.5%, and the second *Brassica* plants produce seeds yielding an oil having an oleic acid content of about 60% to about 74% and an α-linolenic acid content of about 1.9% to about 3.8%; and harvesting $F_1$ hybrid seeds from the first *Brassica* plants, the $F_1$ seeds yielding an oil having an oleic acid content of about 60% to about 70% and an α-linolenic acid content of about 1.6% to about 5.0%. The first *Brassica* plants can be male sterile such as cytoplasmic male sterility (CMS) (e.g., Ogura type CMS). The second *Brassica* plants can include a fertility restorer gene (e.g., of the Kosena or Ogura type). The method further can include planting the $F_1$ hybrid seeds to obtain a plant and harvesting $F_2$ hybrid seeds from the plant, the $F_2$ hybrid seeds having an oleic acid content of about 60% to about 74% and an α-linolenic acid content of about 2.0% to about 5.7% (e.g., 2.5 to 3.5%).

The first *Brassica* plants can produce seeds yielding an oil having an oleic acid content of about 60% to about 65% and an α-linolenic acid content of about 2.5% to about 3.5%. The second *Brassica* plants can produce seeds yielding an oil having an oleic acid content of about 66% to about 73% and an α-linolenic acid content of about 1.5% to about 3.0%.

The first *Brassica* plants further can have decreased delta-12 desaturase D or F activity, wherein the first *Brassica* plants produce seeds yielding an oil having an oleic acid content of about 70% to about 74% and an α-linolenic acid content of about 2.5% to about 3.5%. The second *Brassica* plants can produce seeds yielding an oil having an oleic acid content of about 65% to about 71% and an α-linolenic acid content of about 1.5% to about 3.0%.

The invention also features a method for producing *Brassica* seeds. The method includes growing $F_1$ hybrid plants, such plants produced by hybridizing one or more first *Brassica* plants having decreased delta-15 desaturase activity and one or more second *Brassica* plants having decreased delta-15 desaturase activity, wherein the first *Brassica* plants produce seeds yielding an oil having an oleic acid content of about 60% to about 74% and an α-linolenic acid content of about 0.8% to about 4.5%, and wherein the second *Brassica* plants produce seeds yielding an oil having an oleic acid content of about 60% to about 74% and an α-linolenic acid content of about 1.9% to about 3.8%; and harvesting seeds produced on the $F_1$ hybrid plants, the seeds having an oleic acid content of about 60% to about 70% and an α-linolenic acid content of about 1.6% to about 5.0%.

In another aspect, the invention features a method for producing a hybrid *Brassica* plant. The method includes hybridizing one or more first *Brassica* plants and one or more second *Brassica* plants, the first and second *Brassica* plants containing decreased delta-12 desaturase activity and decreased delta-15 desaturase activity, wherein the first *Brassica* plants produce seeds yielding an oil having an oleic acid content of about 70% to about 85% and an α-linolenic acid content of about 2.0% to about 4.5%, and wherein the second *Brassica* plants produce seeds yielding an oil having an oleic acid content of about 75% to about 85% and an α-linolenic acid content of about 1.5% to about 3.5%; and harvesting $F_1$ hybrid seeds from the first *Brassica* plants, the $F_1$ seeds yielding an oil having an oleic acid content of about 71% to about 80% and an α-linolenic acid content of about 1.5% to about 3.5%. The first *Brassica* plants can be male sterile (e.g., Ogura type CMS). The second *Brassica* plants can include a fertility restorer gene (e.g., of the Kosena or Ogura type). The method further can include planting the $F_1$ hybrid seeds and harvesting $F_2$ hybrid seeds from the $F_1$ plants, the $F_2$ hybrid seeds having an oleic acid content of about 71% to about 80% and an α-linolenic acid content of about 2.0% to about 4.2%.

The first *Brassica* plants can contain a mutation in the fad2-F gene and produce seeds yielding an oil having an oleic acid content of about 75% to about 80% and an α-linolenic acid content of about 2.5% to about 3.5%. The second *Brassica* plants can produce seeds yielding an oil having an oleic acid content of about 75% to about 80% and an α-linolenic acid content of about 2.5% to about 3.5%.

In other embodiments, the first *Brassica* plants can contain a mutation in the fad2-D gene and produce seeds yielding an oil having an oleic acid content of about 75% to about 80% and an α-linolenic acid content of about 2.5% to about 3.5%. The second *Brassica* plants can produce seeds yielding an oil having an oleic acid content of about 75% to about 80% and an α-linolenic acid content of about 2.5% to about 3.5%.

Alternatively, the first *Brassica* plants can contain a mutation in the fad2-D gene and produce seeds yielding an oil having an oleic acid content of about 70% to about 75% and an α-linolenic acid content of about 2.0% to about 3.0%. The second *Brassica* plants can produce seeds yielding an oil having an oleic acid content of about 80% to about 85% and an α-linolenic acid content of about 2.0% to about 2.5%.

In another aspect, the invention features a method for producing *Brassica* seeds. The method includes growing $F_1$ hybrid plants, the plants produced by hybridizing one or more first *Brassica* plants and one or more second *Brassica* plants, the first and second *Brassica* plants having decreased delta-12 desaturase D or F and delta-15 desaturase activities, wherein the first *Brassica* plants produce seeds yielding an oil having an oleic acid content of about 70% to about 85% and an α-linolenic acid content of about 2.0% to about 4.5%, and wherein the second *Brassica* plants produce seeds yielding an oil having an oleic acid content of about 75% to about 85% and an α-linolenic acid content of about 1.5% to about 3.5%; and harvesting seeds produced on the $F_1$ hybrid plants, the seeds having an oleic acid content of about 71% to about 80% and an α-linolenic acid content of about 1.5% to about 3.5%.

In yet another aspect, the invention features a method for producing a hybrid *Brassica* plant. The method includes hybridizing one or more first *Brassica* plants and one or more second *Brassica* plants, the first *Brassica* plants having a decrease in delta-15 desaturase activity, the second *Brassica* plants having a decrease in delta-12 D and F desaturase and delta-15 desaturase activities, wherein the first *Brassica* plants produce seeds yielding an oil having an oleic acid content of about 60% to about 70% and an α-linolenic acid content of about 2.0% to about 4.0%, and wherein the second *Brassica* plants produce seeds yielding an oil having an oleic acid content of about 84% to about 89% and an α-linolenic acid content of about 1.5% to about 2.5%; and harvesting $F_1$ hybrid seeds from the first *Brassica* plants, the $F_1$ seeds yielding an oil having an oleic acid content of about 71% to about 80% and an α-linolenic acid content of about 1.5% to about 4.5%. The first *Brassica* plants can be male sterile (e.g., Ogura type CMS). The second *Brassica* plants can include a fertility restorer gene (e.g., of the Kosena or Ogura type). The method further can include planting the $F_1$ hybrid seeds to obtain a plant and harvesting $F_2$ hybrid seeds from the plant, the $F_2$ hybrid seeds having an oleic acid content of about 71% to about 80% and an α-linolenic acid content of about 1.5% to about 5.0%. The first *Brassica* plants can have a mutation in a fad3 gene and produce seeds yielding an oil having an oleic acid content of about 63% to about 69% and an α-linolenic acid content of about 2.0% to about 2.5%. The second *Brassica* plants can have a mutation in the fad2D and fad2F genes and a mutation in a fad3 gene, wherein the second *Brassica* plants produce seeds yielding an oil having an oleic acid content of about 85% to about 89% and an α-linolenic acid content of about 1.5% to about 2.5%.

The first *Brassica* plants also can have a mutation in the fad2D and fad2F genes and a mutation in a fad3 gene, wherein the second *Brassica* plants produce seeds yielding an oil having an oleic acid content of about 60% to about 65% and an α-linolenic acid content of about 2.5% to about 3.5%. The second *Brassica* plants can have a mutation in the fad2D and fad2F genes and a mutation in a fad3 gene, wherein the second *Brassica* plants produce seeds yielding an oil having an oleic acid content of about 85% to about 89% and an α-linolenic acid content of about 1.5% to about 2.5%. In some embodiments, the first and/or second plants can have two fad3 mutations.

The first *Brassica* plants also can have a mutation in a fad3 gene and produce seeds yielding an oil having an oleic acid content of about 60% to about 65% and an α-linolenic acid content of about 3.0% to about 4.0%. The second *Brassica* plants can have a mutation in the fad2D and fad2F genes and a mutation in a fad3 gene, wherein the second *Brassica* plants produce seeds yielding an oil having an oleic acid content of about 85% to about 89% and an α-linolenic acid content of about 1.5% to about 2.5%. In some embodiments, the first and/or second plants can have two fad3 mutations.

The invention also features a method for producing *Brassica* seeds. The method includes growing $F_1$ hybrid plants, the plants produced by hybridizing one or more first *Brassica* plants and one or more second *Brassica* plants, the first *Brassica* plants having decreased delta-15 desaturase activity, the second *Brassica* plants having decreased delta-12 desaturase D or F and delta-15 desaturase activities, wherein the first *Brassica* plants produce seeds yielding an oil having an oleic acid content of about 60% to about 70% and an α-linolenic acid content of about 2.0% to about 4.5%, and wherein the second *Brassica* plants produce seeds yielding an oil having an oleic acid content of about 84% to about 89% and an α-linolenic acid content of about 1.5% to about 2.5%; and harvesting seeds produced on the $F_1$ hybrid plants, the seeds having an oleic acid content of about 71% to about 80% and an α-linolenic acid content of about 1.5% to about 4.5%.

In another aspect, the invention features a method for producing a hybrid *Brassica* plant. The method includes hybridizing one or more first *Brassica* plants and one or more second *Brassica* plants, the first *Brassica* plants having decreased delta-12 desaturase D or F and decreased delta-15 desaturase activities, the second *Brassica* plants having decreased delta-15 desaturase activity, wherein the first *Brassica* plants produce seeds yielding an oil having an oleic acid content of about 80% to about 86% and an α-linolenic acid content of about 2.0% to about 3.0%, and wherein the second *Brassica* plants produce seeds yielding an oil having an oleic acid content of about 65% to about 70% and an α-linolenic acid content of about 2.0% to about 4.5%; and harvesting $F_1$ hybrid seeds from the first *Brassica* plants, the $F_1$ seeds yielding an oil having an oleic acid content of about 71% to about 80% and an α-linolenic acid content of about 1.5% to about 4.5%. The first *Brassica* plants can be male sterile (e.g., CMS of the Ogura type). The second *Brassica* plants can include a fertility restorer gene (e.g., of the Kosena or Ogura type). The method further can include planting the $F_1$ hybrid seeds to obtain a plant and harvesting $F_2$ hybrid seeds from the plant, the $F_2$ hybrid seeds having an oleic acid content of about 71% to about 80% and an α-linolenic acid content of about 1.5% to about 5.0%.

In yet another aspect, the invention features a method for producing a hybrid *Brassica* plant. The method includes hybridizing one or more first *Brassica* plants and one or more second *Brassica* plants, the first and second *Brassica* plants containing decreased delta-12 desaturase D or F and delta-15 desaturase activities, wherein the first *Brassica* plants produce seeds yielding an oil having an oleic acid content of about 81% to about 89% and an α-linolenic acid content of about 1.5% to about 4.5%, and wherein the second *Brassica* plants produce seeds yielding an oil having an oleic acid content of about 81% to about 89% and an α-linolenic acid content of about 1.5% to about 3.6%; and harvesting $F_1$ hybrid seeds from the first *Brassica* plants, the $F_1$ seeds yielding an oil having an oleic acid content of about 81% to about 86% and an α-linolenic acid content of about 1.5% to about 4.0%. The first *Brassica* plants can be male sterile (e.g., CMS of the Ogura type). The second *Brassica* plants can include a fertility restorer gene (e.g., of the Kosena or Ogura type). The method further includes planting the $F_1$ hybrid seeds to obtain a plant and harvesting $F_2$ hybrid seeds from the plant, the $F_2$ hybrid seeds having an oleic acid content of about 81% to about 86% and an α-linolenic acid content of about 1.5% to about 5.0%.

The invention also features a method for producing *Brassica* seeds. The method includes growing $F_1$ hybrid plants, the plants produced by hybridizing one or more first *Brassica* plants and one or more second *Brassica* plants, the first and second *Brassica* plants having decreased delta-12 D and F desaturase and delta-15 desaturase activities, wherein the first *Brassica* plants produce seeds yielding an oil having an oleic acid content of about 81% to about 89% and an α-linolenic acid content of about 1.5% to about 4.5%, and wherein the second *Brassica* plants produce seeds yielding an oil having an oleic acid content of about 81% to about 89% and an α-linolenic acid content of about 1.5% to about 3.6%; and harvesting seeds produced on the $F_1$ hybrid plants, the seeds having an oleic acid content of about 81% to about 86% and an α-linolenic acid content of about 1.5% to about 4.0%.

In another aspect, the invention features a canola oil having an oleic acid content from about 71% to about 80% (e.g., about 71.5% to about 78%, 71% to 74%, or about 75% to about 80%) and an α-linolenic acid content from about 2.0% to about 4.2% (e.g., about 2.1% to about 2.9%, or about 2.5% to about 3.5%), an OLO content from about 22% to about 36% (e.g., about 23% to about 27%) and an OOO content from about 51% to about 69% (e.g., about 60% to about 68% or about 63% to about 67%). The canola oil can have an LLO content from 2% to about 5% (e.g., 2.1%).

The invention also features a canola oil having an oleic acid content from about 71% to about 80% (e.g., about 73% to about 78%) and an α-linolenic acid content from about 1.5% to about 4.5% (e.g., about 2.1% to about 2.9%), an OLO content from about 11% to about 17% (e.g., about 14% to about 17%) and an OOO content from about 74% to about 82% (e.g., about 75% to about 80%). The canola oil can have an LLO content from about 0.4% to about 1.5% (e.g., 0.7% to 0.8%).

Canola oil having an oleic acid content from about 81% to about 86% (e.g., about 81% to about 83%, about 82% to about 85%, or about 83% to about 86%) and an α-linolenic acid content from about 1.5% to about 4.0% (e.g., about 2.3% to about 3.5%) also is featured. Such oil has an OLO content from about 4% to about 7% (e.g., about 5% to about 6%) and an OOO content from about 85% to about 90% (e.g., about 85% to about 88%).

In another aspect, the invention features a method for producing canola oil. The method includes growing $F_1$ hybrid *Brassica* plants, the plants produced by hybridizing one or more first *Brassica* plants and one or more second *Brassica* plants, the first *Brassica* plants having decreased delta-15 desaturase activity, the second *Brassica* plants having decreased delta-12 desaturase D or F and delta-15 desaturase activities, wherein the first *Brassica* plants produce seeds yielding an oil having an oleic acid content of about 60% to about 70% and an α-linolenic acid content of about 2.0% to about 4.5%, and wherein the second *Brassica* plants produce seeds yielding an oil having an oleic acid content of about 84% to about 89% and an α-linolenic acid content of about 1.5% to about 2.5%; harvesting seeds produced on the $F_1$ hybrid plants; and extracting oil from the harvested seeds, the seeds having an oleic acid content of about 71% to about 80% and an α-linolenic acid content of about 1.5% to about 4.5%, and an OLO content of about 11% to about 17% and an OOO content of about 74% to about 82%. The first *Brassica* plants can be male sterile (e.g., CMS such as Ogura type CMS) and the second *Brassica* plants can include a fertility restorer gene (e.g., Kosena or Ogura type).

In some embodiments, the first *Brassica* plants can have a mutation in a fad3 gene and produce seeds yielding an oil having an oleic acid content of about 63% to about 69% and an α-linolenic acid content of about 2.0% to about 2.5%. The second *Brassica* plants can have a mutation in the fad2D and fad2F genes and a mutation in a fad3 gene, and produce seeds yielding an oil having an oleic acid content of about 85% to about 89% and an α-linolenic acid content of about 1.5% to about 2.5%. The first and/or second plants can have two fad3 mutations.

In other embodiments, the first *Brassica* plants can have a mutation in the fad2D and fad2F genes and a mutation in a fad3 gene, and produce seeds yielding an oil having an oleic acid content of about 60% to about 65% and an α-linolenic acid content of about 2.5% to about 3.5%. The second *Brassica* plants can have a mutation in the fad2D and fad2F genes and a mutation in a fad3 gene, and produce seeds yielding an oil having an oleic acid content of about 85% to about 89% and an α-linolenic acid content of about 1.5% to about 2.5%. The first and/or second plants can have two fad3 mutations.

In still other embodiments, the first *Brassica* plants can have a mutation in a fad3 gene and produce seeds yielding an oil having an oleic acid content of about 60% to about 65% and an α-linolenic acid content of about 3.0% to about 4.0%. The second *Brassica* plants can have a mutation in the fad2D and fad2F genes and a mutation in a fad3 gene, and produce seeds yielding an oil having an oleic acid content of about 85% to about 89% and an α-linolenic acid content of about 1.5% to about 2.5%. The first and/or second plants can have two fad3 mutations.

In another aspect, the invention features a method for producing canola oil. The method includes growing $F_1$ hybrid *Brassica* plants, the plants produced by hybridizing one or more first *Brassica* plants and one or more second *Brassica* plants, the first *Brassica* plants having decreased delta-12 desaturase D or F and decreased delta-15 desaturase activities, the second *Brassica* plants having decreased delta-15 desaturase activity, wherein the first *Brassica* plants produce seeds yielding an oil having an oleic acid content of about 80% to about 86% and an α-linolenic acid content of about 2.0% to about 3.0%, and wherein the second *Brassica* plants produce seeds yielding an oil having an oleic acid content of about 65% to about 70% and an α-linolenic acid content of about 2.0% to about 4.5%; harvesting seeds produced on the $F_1$ hybrid plants; and extracting oil from the harvested seeds, the seeds having an oleic acid content of about 71% to about 80% and an α-linolenic acid content of about 1.5% to about 4.5%, and an OLO content of about 11% to 17% and an OOO content of about 74% to about 82%. The first *Brassica* plants can be male sterile (e.g., CMS such as Ogura type CMS). The second *Brassica* plants can include a fertility restorer gene (e.g., Kosena or Ogura type).

In yet another aspect, the invention features a method for producing canola oil that includes growing $F_1$ hybrid plants, the plants produced by hybridizing one or more first *Brassica* plants having decreased delta-15 desaturase activity and one or more second *Brassica* plants having decreased delta-15 desaturase activity, wherein the first *Brassica* plants produce seeds yielding an oil having an oleic acid content of about 60% to about 74% and an α-linolenic acid content of about 0.8% to about 4.5%, and the second *Brassica* plants produce seeds yielding an oil having an oleic acid content of about 60% to about 74% and an α-linolenic acid content of about 1.9% to about 3.8%; harvesting seeds produced on the $F_1$ hybrid plants; and extracting oil from the seeds. The seeds yield an oil having an oleic acid content of about 71 to 80% and an α-linolenic acid content of about 2.0 to 4.2%, wherein the OLO content of the oil is from about 22% to about 36% and the OOO content is from about 51% to about 69%. The first Brassica plants can be male sterile (e.g., CMS such as Ogura type CMS). The second Brassica plants can include a fertility restorer gene (e.g., Kosena or Ogura type).

In another aspect, the invention features a method for producing canola oil. The method includes growing $F_1$ hybrid plants, the plants produced by hybridizing one or more first Brassica plants and one or more second Brassica plants, the first and second Brassica plants having decreased delta-12 D and F desaturase and delta-15 desaturase activities, wherein the first Brassica plants produce seeds yielding an oil having an oleic acid content of about 81% to about 89% and an α-linolenic acid content of about 1.5% to about 4.5%, and the second Brassica plants produce seeds yielding an oil having an oleic acid content of about 81% to about 89% and an α-linolenic acid content of about 1.5% to about 3.6%; harvesting seeds produced on the $F_1$ hybrid plants; and extracting oil from the seeds. The seeds yield an oil having an oleic acid content of about 81% to about 86% and an α-linolenic acid content of about 1.5 to about 4.0%, wherein the OLO content of the oil is from about 4% to about 7% and the OOO content is from about 85% to about 90%. The first Brassica plants can be male sterile (e.g., CMS such as Ogura type CMS). The second Brassica plants can include a fertility restorer gene (e.g., Kosena or Ogura type).

The invention also features a food composition that includes a canola oil described above. The food composition can be a bakery product such as a cookie, muffin, pie filling, pastry, pie crust, doughnut, bread, or cake. The food composition also can be a cracker, a breakfast cereal, a breakfast bar, or a fried food (e.g., a snack chip such as a corn chip or potato chip, or a French fry).

In another embodiment, the invention features a spray coating that includes a canola oil described above. The spray coating further can include another vegetable oil (e.g., cottonseed, soybean, corn, or sunflower oil). The spray coating also can include an antioxidant and/or a seasoning.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
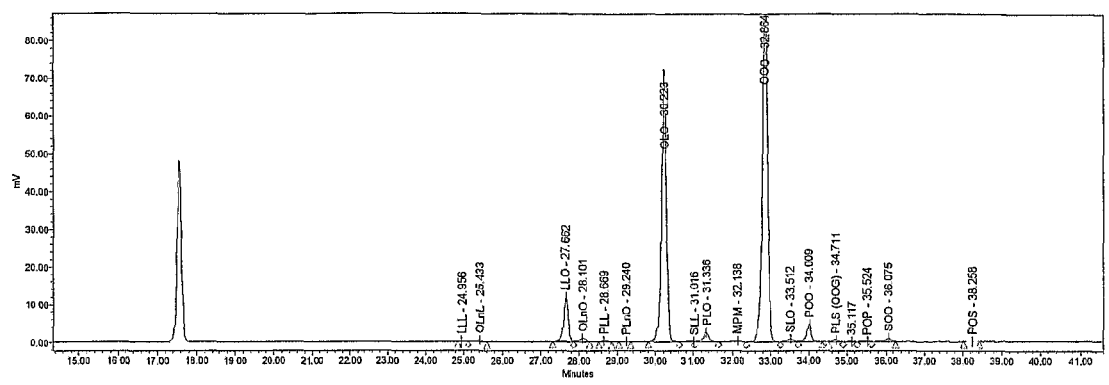
FIG. 1 is a chromatogram of the triacylglycerol (TAG) profile of CV65 oil. The internal standard peak is at 17.5 min.

In general, the invention provides methods for producing hybrid Brassica varieties, including B. napus, B. juncea, and B. rapa species of Brassica, that yield seeds having a low linolenic acid content (<6%) in combination with a low (60%-70%), mid (70%-80%), or high (>80%) oleic acid content. Such hybrid Brassica varieties can produce seed oils having a fatty acid content tailored to the desired end use of the oil. For example, hybrid Brassica varieties can be produced that yield seeds having an oleic acid content of 60% to 74% and an α-linolenic acid content of 1.5% to 4.0%. Total polyunsaturates (i.e., total of linoleic acid and α-linolenic acid) in such seeds typically is <26%. Canola oils having such fatty acid contents are particularly useful for frying applications due to the polyunsaturated content, which is low enough to have improved oxidative stability for frying yet high enough to impart the desired fried flavor to the food being fried, and are an improvement over commodity type canola oils. The fatty acid content of commodity type canola oils typically is about 60% oleic acid, about 7-9% α-linolenic acid, and about 30% total polyunsaturates.

Hybrid Brassica varieties can be produced that yield seeds having a mid oleic acid content (e.g., 71% to 80% oleic acid) and a low α-linolenic acid content (e.g., 1.5% to 4.0%). Canola oils having such fatty acid contents have an oxidative stability that is higher than oils with a lower oleic acid content or commodity type canola oils, and are useful for coating applications (e.g., spray-coatings), formulating food products, or other applications where shelf-life stability is desired. In addition, hybrid Brassica varieties can be produced that yield seeds having a high oleic acid content (e.g., 81% to 89% oleic acid) and an α-linolenic acid content of 1.5% to 3.0%. Canola oil having a high oleic acid and low α-linolenic acid content is particularly useful for food and industrial (e.g., as lubricating or slip agents) applications requiring high oxidative stability.

Canola oil obtained from such hybrid Brassica varieties can have an altered TAG composition and/or TAG structure relative to the TAG composition and/or structure from a canola oil having a similar fatty acid content, but obtained from a non-hybrid Brassica variety. TAG composition refers to the type and amount of TAG in the oil, while TAG structure refers to the location of the fatty acid on the glycerol moiety. An altered TAG composition and/or structure can result in the canola oil having increased oxidative stability, flavor stability, and/or color stability. For example, an increased proportion of oleic acid and/or a decreased proportion of linoleic acid at carbon 2 of the glycerol moiety relative to the proportion in known oils can result in canola oil having increased oxidative stability. TAGs are identified herein by a three-letter acronym representing the respective fatty acids and their order in the molecule. "L" stands for linoleic acid; "Ln" stands for α-linolenic acid; "O" stands for oleic acid; "P" stands for palmitic acid; and "S" stands for stearic acid. For example, triolein is represented by OOO.

Production of Hybrid Brassica Varieties

Hybrid Brassica varieties can be produced by preventing self-pollination of female parent plants (i.e., seed parents), permitting pollen from male parent plants to fertilize female parent plant, and allowing $F_1$ hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be cytoplasmic male sterility (CMS), nuclear male sterility, genetic male sterility, molecular male sterility wherein a transgene inhibits microsporogenesis and/or pollen formation, or be produced by self-incompatibility. Female parent plants containing CMS are particularly useful. CMS can be, for example of the ogu (Ogura), nap, pol, tour, or mur type. See, for example, Pellan-Delourme and Renard, 1987, *Proc. 7th Int. Rapeseed Conf.*, Poznan, Poland, p. 199-203 and Pellan-Delourme and Renard, 1988, *Genome* 30:234-238, for a description of Ogura type CMS. See, Riungu and McVetty, 2003, *Can. J. Plant Sci.*, 83:261-269 for a description of nap, pol, tour, and mur type CMS.

In embodiments in which the female parent plants are CMS, the male parent plants typically contain a fertility restorer gene to ensure that the $F_1$ hybrids are fertile. For example, when the female parent contains an Ogura type CMS, a male parent is used that contains a fertility restorer gene that can overcome the Ogura type CMS. Non-limiting examples of such fertility restorer genes include the Kosena type fertility restorer gene (U.S. Pat. No. 5,644,066) and Ogura fertility restorer genes (U.S. Pat. Nos. 6,229,072 and 6,392,127). In other embodiments in which the female parents are CMS, male parents can be used that do not contain a fertility restorer. $F_1$ hybrids produced from such parents are male sterile. Male sterile hybrid seed can be inter-planted with male fertile seed to provide pollen for seed-set on the resulting male sterile plants.

The methods of the invention can be used to form single-cross *Brassica* $F_1$ hybrids. In such embodiments, the parent plants can be grown as substantially homogeneous adjoining populations to facilitate natural cross-pollination from the male parent plants to the female parent plants. The $F_1$ seed formed on the female parent plants is selectively harvested by conventional means. One also can grow the two parent plants in bulk and harvest a blend of $F_1$ hybrid seed formed on the female parent and seed formed upon the male parent as the result of self-pollination. Alternatively, three-way crosses can be carried out wherein a single-cross $F_1$ hybrid is used as a female parent and is crossed with a different male parent that satisfies the fatty acid parameters for the female parent of the first cross. Here, assuming a bulk planting, the overall oleic acid content of the vegetable oil may be reduced over that of a single-cross hybrid; however, the seed yield will be further enhanced in view of the good agronomic performance of both parents when making the second cross. As another alternative, double-cross hybrids can be created wherein the $F_1$ progeny of two different single-crosses are themselves crossed. Self-incompatibility can be used to particular advantage to prevent self-pollination of female parents when forming a double-cross hybrid.

Hybrids described herein have good agronomic properties and exhibit hybrid vigor, which results in seed yields that exceed that of either parent used in the formation of the $F_1$ hybrid. For example, yield can be at least 10% (e.g., 10% to 20%, 10% to 15%, 15% to 20%, or 25% to 35%) above that of either one or both parents. In some embodiments, the yield exceeds that of open-pollinated spring canola varieties such as 46A65 (Pioneer) or Q2 (University of Alberta), when grown under similar growing conditions. For example, yield can be at least 10% (e.g., 10% to 15% or 15% to 20%) above that of an open-pollinated variety.

Hybrids described herein typically produce seeds having very low levels of glucosinolates (<30 μmol/gram of de-fatted meal at a moisture content of 8.5%). In particular, hybrids can produce seeds having <20 μmol of glucosinolates/gram of de-fatted meal. As such, hybrids can incorporate mutations or transgenes that confer low glucosinolate levels. See, for example, U.S. Pat. No. 5,866,762. Glucosinolate levels can be determined in accordance with known techniques, including high performance liquid chromatography (HPLC), as described in ISO 9167-1:1992(E), for quantification of total, intact glucosinolates, and gas-liquid chromatography for quantification of trimethylsilyl (TMS) derivatives of extracted and purified desulfoglucosinolates. Both the HPLC and TMS methods for determining glucosinolate levels analyze de-fatted or oil-free meal.

Parent Plants

Suitable parent plants for making hybrid varieties of the invention have low linolenic acid in the seed oil as a result of decreased activity of delta-15 desaturase (also known as FAD3), which is involved in the enzymatic conversion of linoleic acid to α-linolenic acid. The gene encoding delta-15 fatty acid desaturase is referred to as fad3 in *Brassica* and *Arabidopsis*. Many *Brassica* species are amphidiploids, and as a result, have fad3 genes derived from each ancestral genome that make up such *Brassica* species. Sequences of higher plant fad3 genes are disclosed in Yadav et al., *Plant Physiol.*, 103:467-476 (1993), WO 93/11245, and Arondel et al., *Science*, 258:1353-1355 (1992). Decreased activity, including absence of detectable activity, of delta-15 desaturase can be achieved by techniques such as mutagenesis, antisense suppression, ribozyme cleavage, dominant negative suppression, co-suppression, or RNA interference (RNAi) technology. Decreased activity, including absence of detectable activity, can be inferred from the decreased level of linolenic acid (product) and in some cases, increased level of linoleic acid (the substrate) in the plant compared with a corresponding control plant.

Expression of delta-15 desaturase can be decreased using antisense technology. The specific hybridization of a fad3 antisense molecule with endogenous fad3 nucleic acids can interfere with the normal function of the endogenous nucleic acid. When the endogenous nucleic acid is DNA, antisense technology can disrupt replication and transcription. When the endogenous nucleic acid is RNA, antisense technology can disrupt, for example, translocation of the RNA to the site of protein translation, translation of protein from the RNA, splicing of the RNA to yield one or more mRNA species, and catalytic activity of the RNA. Antisense technology also can facilitate nucleolytic degradation of an endogenous RNA. See, for example, Brantl, 2002, *Biochim. Biophys. Acta*, 1575:15-25 and Sazani et al., 2002, *Curr. Opin. Biotechnol.*, 13:468-72. Antisense molecules can be directed at regions encompassing the translation initiation or termination codon of fad3. Antisense molecules also can be directed at the fad3 open reading frame (ORF), at the 5' and 3' untranslated region of fad3, and at intron regions and intron-exon junction regions. The effectiveness of an antisense molecule to decrease expression of fad3 can be evaluated by measuring levels of the fad3 mRNA or protein (e.g., by Northern blotting, RT-PCR, Western blotting, ELISA, or immunohistochemical staining).

The term "hybridization," as used herein with respect to antisense technology, means hydrogen bonding, which can be Watson-Crick, Hoogsteen, or reversed Hoogsteen hydrogen bonding, between complementary nucleotides. It is understood in the art that the sequence of a fad3 antisense molecule need not be 100% complementary to that of its endogenous fad3 nucleic acid to be able to hybridize. A fad3 antisense molecule specifically hybridizes to an endogenous fad3 nucleic acid when (a) binding of the antisense molecule to the fad3 DNA or RNA molecule, respectively, interferes with the normal function of the fad3 DNA or RNA, respectively, and (b) there is sufficient complementarity to avoid non-specific binding of the antisense molecule to non-fad3 sequences, respectively, under conditions in which specific binding is desired, i.e., under conditions in which in vitro assays are performed or under physiological conditions for in vivo assays. In some embodiments, it may be useful to design multiple antisense molecules that each hybridize to a different region of fad3. In such embodiments, multiple antisense molecules can be on the same construct or on different constructs.

Ribozyme molecules can be designed to cleave delta-15 desaturase mRNA transcripts and prevent expression of delta-15 desaturase. While various ribozymes that cleave mRNA at site-specific recognition sequences can be used to destroy desaturase mRNAs, hammerhead ribozymes are particularly useful. Hammerhead ribozymes cleave mRNAs at locations dictated by flanking regions that form complementary base pairs with the target mRNA. The sole requirement is that the target RNA contain a 5'-UG-3' nucleotide sequence. The construction and production of hammerhead ribozymes is well known in the art. See, for example, U.S. Pat. No. 5,254,678. Hammerhead ribozyme sequences can be embedded in a stable RNA such as a transfer RNA (tRNA) to increase cleavage efficiency in vivo. Perriman, R. et al., *Proc. Natl. Acad. Sci. USA*, 92(13):6175-6179 (1995); de Feyter, R. and Gaudron, J., *Methods in Molecular Biology*, Vol. 74, Chapter 43, "Expressing Ribozymes in Plants", Edited by Turner, P. C, Humana Press Inc., Totowa, N.J. RNA endoribonucleases such as the one that occurs naturally in *Tetrahyinena thermophila*, and which have been described extensively by Cech and collaborators are also useful. See, for example, U.S. Pat. No. 4,987,071.

The expression of fad3 can be decreased using co-suppression technology. Co-suppression is a reduction in expression of a target gene upon introduction into a cell of a nucleic acid that is ultimately transcribed into an mRNA that has homology with the target gene's transcript. Therefore, co-suppression of fad3 can be achieved using a construct that contains a fad3 nucleic acid, respectively, operably linked in sense orientation to a regulatory element. It is not necessary that the fad3 nucleic acid in the construct be full-length or have 100% homology with the target fad3 nucleic acid, respectively, to be co-suppressed. See, for example, U.S. Pat. Nos. 5,034,323 and 5,231,020 for a description of co-suppression technology.

Regulatory sequences typically do not themselves code for a gene product. Instead, regulatory sequences affect the expression level of the coding sequence. Examples of regulatory sequences are known in the art and include, without limitation, promoters of genes expressed during embryogenesis, e.g., a napin promoter, a phaseolin promoter, an oleosin promoter, a cruciferin promoter and constitutive promoters such as the cauliflower mosaic virus 35S promoter. Native regulatory sequences, including the native promoters of fad3 genes also can be used in constructs of the invention. Other examples of suitable regulatory sequences include enhancers or enhancer-like elements, inducible elements, introns and 3' non-coding regions such as poly A sequences. Further examples of suitable regulatory sequences for the proper expression of fad3 coding sequences are known in the art.

In another alternative, the transgene can include a sequence that is transcribed into an interfering RNA. Such an RNA can be one that can anneal to itself, e.g., a double stranded RNA having a stem-loop structure. One strand of the stem portion of a double stranded RNA comprises a sequence that is similar or identical to the sense coding sequence of an endogenous delta-15 desaturase, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises an antisense sequence of an endogenous delta-15 desaturase, and can have a length that is shorter, the same as, or longer than the corresponding length of the sense sequence. The loop portion of a double stranded RNA can be from 10 nucleotides to 5,000 nucleotides, e.g., from 15 nucleotides to 1,000 nucleotides, from 20 nucleotides to 500 nucleotides, or from 25 nucleotides to 200 nucleotides in length. The loop portion of the RNA can include an intron. RNAi technology utilizes constructs that produce aberrant RNA transcripts, which disrupt transcription and/or translation of the endogenous fad3. See, for example, U.S. Pat. No. 6,506,559; WO 99/53050; WO 01/12824; and WO 01/29058 for a description of RNAi technology and its use in decreasing expression of an endogenous nucleic acid.

Mutagenesis also can be used to decrease delta-15 desaturase activities. Mutagenic agents can be used to induce random genetic mutations within a population of seeds or regenerable plant tissue. Suitable mutagenic agents include, for example, ethyl methane sulfonate, methyl N-nitrosoguanidine, ethidium bromide, diepoxybutane, x-rays, UV rays and other mutagens known in the art. The treated population, or a subsequent generation of that population, is screened for reduced desaturase activity that results from the mutation. Mutations can be in any portion of a gene, including coding sequence, intron sequence and regulatory elements, that render the resulting gene product non-functional or with reduced activity. Suitable types of mutations include, for example, insertions or deletions of nucleotides, and transitions or transversions in the wild-type coding sequence. Such mutations can lead to deletion or insertion of amino acids, and conservative or non-conservative amino acid substitutions in the corresponding gene product.

Parent plants can contain the mutation from the APOLLO or STELLAR *B. napus* variety that confers low linolenic acid. The STELLAR and APOLLO varieties were developed at the University of Manitoba (Manitoba, Canada). In some embodiments, the parents contain the mutation from IMC01 or mutations from IMC02 that confer a low linolenic acid phenotype. The mutation(s) are thought to be in fad3 genes. IMC01 was deposited with the American Type Culture Collection (ATCC) under Accession No. 40579. IMC02 was deposited with the ATCC under Accession No. PTA-6221. See U.S. Pat. No. 5,750,827 for a description of IMC01 and IMC02.

Suitable parent plants also can have decreased activity of a delta-12 desaturase, which is involved in the enzymatic conversion of oleic acid to linoleic acid, to confer a mid or high oleic acid content in the seed oil. *Brassica* species also have more than one fad2 gene. The sequences for the wild-type fad2 genes from *B. napus* (termed the D form and the F form) are disclosed in WO 98/56239. A reduction in delta-12 desaturase activity, including absence of detectable activity, can be achieved by techniques including, but not limited to, mutagenesis, antisense suppression, ribozyme cleavage, dominant negative suppression, co-suppression, or RNAi technology, as described above. Decreased delta-12 desaturase activity can be inferred from the decrease level of linoleic acid (product) and increased level of oleic acid (substrate) in the plant compared with a corresponding control plant.

Non-limiting examples of suitable fad2 mutations include the G to A mutation at nucleotide 316 within the fad2-D gene, which results in the substitution of a glutamic acid residue for leucine in the protein. Such a mutation is found within the variety IMC129, which has been deposited with the ATCC under Accession No. 40811. Another suitable fad2 mutation can be the T to A mutation at nucleotide 515 of the fad2-F gene, which results in the substitution of a leucine residue for histidine in the protein. Such a mutation is found within the variety Q4275, which has been deposited with the ATCC under Accession No. 97569. See U.S. Pat. No. 6,342,658. Typically, the presence of one of the fad2-D or fad2-F mutations confers a mid-oleic acid phenotype (e.g., 70-80% oleic acid) to the seed oil. Q4275 also contains the fad2-D mutation from IMC129. The presence of both fad2 mutations in Q4275 confers a high oleic acid phenotype of greater than 80%.

It is noted that combinations of techniques can be used to obtain the desired oil profile in the $F_1$ hybrid. For example, one parent can have a decreased linolenic acid seed content as a result of a fad3 mutation, while the other parent can have a low linolenic, mid-oleic acid seed content as a result of transgenic techniques.

Production of Hybrid Varieties Yielding Seeds with Low to Mid Oleic Acid and Low Linolenic Acid For production of hybrid varieties that yield seed having a low- to mid-level of oleic acid (e.g., 60 to 74%) and a low linolenic acid content, each parent typically contains decreased delta-15 desaturase activity as discussed above. For example, each parent plant can have the mutation from IMC01 or mutations from IMC02 that confer a low linolenic acid phenotype. Parent plants that are suitable for production of low to mid oleic acid and low linolenic acid yielding varieties have an oleic acid content of about 60% to 74% (e.g., 60% to 65%, 65% to 71%, 66% to 73%) and an α-linolenic acid content of 0.8% to 4.9% (e.g., 1.5% to 4.9%, 1.5% to 4.0%, 1.5% to 3.5%, 1.5% to 3.0%, 1.5% to 2.5%, 1.9% to 3.8%, or 2.5% to 3.5%) in the seed oil. $F_1$ hybrids that result from a cross of such parents typically yield seeds having an oleic acid content of about 60% to 74% and an α-linolenic acid content of about 1.5% to 5.0% (e.g., 1.6% to 5.0%, 2.0% to 3.0%, 2.0% to 3.5%, or 2.5% to 3.5%). See, Example 1A of Table 1. Upon planting such $F_1$ hybrid seed, the resulting plants yield $F_2$ seed having an oleic acid content of 60% to 70% and an α-linolenic acid content of 2.0% to 5.7% (e.g., 2.5% to 3.5%).

In some embodiments, the male or female parent plant has a mid-oleic acid and low linolenic acid seed composition as a result of decreased delta-12 and delta-15 desaturase activities. For example, the male or female parent plant can have decreased activity of the D or F form of delta-12 desaturase. Such plants can produce seeds having an oleic acid content of about 70% to 74% (e.g., 71% to 73%) and an α-linolenic acid content of 1.5% to 4.0% (e.g., 1.5% to 3.0%). For example, a suitable parent can have a mutation within a fad2 gene and a fad3 gene. $F_1$ hybrids that result from a cross of a fad2 and fad3 mutant parent and a fad3 mutant parent typically have an oleic acid content of about 66% to 74% and an α-linolenic acid content of about 1.5% to 3.5% (e.g., 1.5% to 3.0% or 2.0% to 3.5%) in the seed oil. See, Example 1B of Table 1. $F_1$ hybrid seed can be planted and the $F_2$ seed can be harvested from the resulting plants. Typically, the $F_2$ seed will have an oleic acid content of 60% to 70% oleic acid and an α-linolenic acid content of 2.0% to 5.7% (e.g., 2.5% to 3.5%).

Production of Hybrid Varieties Yielding Seeds with Mid Oleic Acid and Low Linolenic Acid For production of hybrid varieties that yield seed having a mid level of oleic acid (e.g., 71 to 80%) and a low linolenic acid content (e.g., 6% or less), a variety of parents can be used. In one embodiment, the parent plants each can produce seeds having about 70% to 80% oleic acid (e.g., 72% to 76%, 73% to 77%, or 75% to 80%) and about 1.5% to 4.5% α-linolenic acid (e.g., 1.5% to 3.5%, or 2.0% to 4.5%) and are crossed to obtain a mid-oleic acid and low linolenic acid oil composition in the seeds. In another embodiment, one parent produces seeds having an oleic acid content of about 60% to 74% and an α-linolenic acid content of about 0.8% to about 4.9%, and the other parent has a mid oleic acid content (e.g., 70% to 80%) and a low α-linolenic acid content (e.g., about 1.5% to 4.5%). Parent plants having a mid-oleic acid, low linolenic acid seed composition typically contain a fad2 mutation and at least one fad3 mutation. Suitable fad2 and fad3 mutations are described above. For example, a parent plant can have the fad2-D mutation from IMC129 or fad2-F mutation from Q4275 and the fad3 mutation from IMC01 or fad3 mutations from IMC02. $F_1$ hybrids that result from a cross of two parents that each contain a fad2 and fad3 mutation typically have an oleic acid content of about 71% to 80% (e.g., 71.5% to 78% or 73% to 77%) and an α-linolenic acid content of about 1.5% to 3.5% (e.g., 2.0% to 3.0% or 2.1% to 2.9%). See, Examples 2A and 2B of Table 2. $F_1$ seeds can be planted and the $F_2$ seed harvested from the resulting plants. Typically, the $F_2$ seed has an oleic acid content of 71% to 80% (e.g., 71% to 74% or 75% to 80%) and an α-linolenic acid content of 2.0% to 4.2% (e.g., 2.0% to 3.5%, 2.1% to 2.9%, or 2.5% to 3.5%). The OLO content of the oil can range from about 22% to about 36% (e.g., 23% to 27%) and the OOO content can range from about 51% to about 69% (e.g., 60% to 68% or 63% to 67%). The LLO content can range from 2% to about 5% (e.g., 2.1%). See, for example, line 03H259 of Tables 12 and 13.

In other embodiments, one parent plant has a low oleic acid seed composition (e.g., 60% to 70%, 60% to 65%, or 63% to 69% oleic acid) and low linolenic acid composition and the other parent plant has a high oleic acid (e.g., 81% to 89% or 85% to 89% oleic acid) and a low linolenic acid seed composition (e.g., 1.5% to 4.5%, 1.5% to 2.5%, 2.0% to 4.0%, 2.5% to 3.5%, or 3.0% to 4.0%). For example, the female parent can have the low oleic, low linolenic seed composition and the male parent can have the high oleic acid, low linolenic acid seed composition. Alternatively, the female parent can have the high oleic acid, low linolenic acid seed composition and the male parent can have the low oleic acid, low linolenic acid seed composition. Parent plants having a low oleic acid, low linolenic acid seed composition typically contain at least one fad3 mutation, while parent plants having a high oleic acid, low linolenic acid seed composition typically contain at least one fad3 mutation and two different fad2 mutations. The combination of two fad2 mutations results in a high oleic acid seed oil composition. For example, the parent plant can contain both fad2 mutations from Q4275. $F_1$ hybrids that result from a cross of such parent plants typically have an oleic acid content of about 71% to 80% (e.g., 72% to 78% or 73% to 77%) and an α-linolenic acid content of about 1.5% to 4.5% (e.g., 1.5% to 3.5%). See, Example 3A of Table 3, Examples 4A and 4B of Table 4, and Examples 5A and 5B of Table 5. Upon planting such $F_1$ hybrid seed, the resulting plants yield $F_2$ seed having an oleic acid content of 71% to 80% and an α-linolenic acid content of 1.5% to 5.0% (e.g., 1.5% to 3.5%, 2.0% to 5.0%, or 2.5% to 4.5%). The OLO content of such oils can range from about 11% to 17% (e.g., 14% to 17%) and the OOO content can range from about 74% to about 82% (e.g., 75% to 80%). The LLO content can range from about 0.4% to about 1.5% (e.g., 0.7% to 0.8%).

In still other embodiments, one parent plant has a mid-oleic acid, low linolenic acid seed composition and the other parent has a high oleic acid, low linolenic acid seed composition. For example, one parent plant can contain a fad2 mutation (e.g., the fad2-D or fad2-F mutation described above) and one or two fad3 mutations and the other parent plant can contain two fad2 mutations (e.g., the fad2-D and fad2-F mutations from Q4275) and one or two fad3 mutations. $F_1$ hybrids that result from a cross of such parent plants typically have an oleic acid content of 71 to 80% and an α-linolenic acid content of 1.5 to 3.5% (e.g., 2.0 to 3.0%). See, Example 3B of Table 3. Such $F_1$ hybrid seed can be planted and $F_2$ seed harvested from the resulting plant. $F_2$ seed generally has an oleic acid content of 71 to 80% (e.g., 73% to about 78%) and an α-linolenic acid content of 1.5 to 4.2% (e.g., 2.0 to 4.2%, 2.0 to 3.5%, 2.1 to 2.9%, or 2.5 to 3.5%). The OLO content of such oils can range from about 11% to 17% (e.g., 14% to 17%) and the OOO content can range from about 74% to about 82% (e.g., 75% to 80%). The LLO content can range from about 0.4% to about 1.5% (e.g., 0.7% to 0.8%).

Production of Hybrid Varieties Yielding Seeds with High Oleic Acid and Low Linolenic Acid Typically, hybrid varieties yielding a high oleic acid, low linolenic acid seed oil composition are produced using two high oleic acid parent plants. For example, each parent plant can include two different fad2 mutations and one or two fad3 mutations. $F_1$ hybrids that result from a cross of such parent plants typically have an oleic acid content of about 81 to 86% (e.g., 81 to 83%, 82 to 85%, or 83 to 86%) and an α-linolenic acid content of about 1.5 to 4.0% (e.g., 1.5 to 3.5%, 2.0 to 3.0%, 2.3 to 3.5%, or 2.8 to 3.4%). See Examples 6A and 6B of Table 6 and Example 10, Tables 15-17. The OLO content can range from about 4% to about 7% (e.g., about 5% to about 6%) and an OOO content can range from about 85% to 90% (e.g., about 85 to about 88%).

Canola Oil

The fatty acid composition of seeds can be determined by first crushing and extracting oil from bulk seed samples (e.g., 10 or more seeds). TAGs in the seed are hydrolyzed to produce free fatty acids, which then can be converted to fatty acid methyl esters and analyzed using techniques known to the skilled artisan, e.g., gas-liquid chromatography (GLC). Near infrared (NIR) analysis can be performed on whole seed according to AOCS Procedure Am-192 (revised 1999).

Hybrid varieties disclosed herein are useful for producing a harvested crop that can be used to make a crude canola oil or a refined, bleached, and deodorized canola oil. For example, $F_1$ hybrid seed harvested from female plants can be planted and $F_2$ seed harvested from the resulting plants. Harvested canola seed can be crushed by techniques known in the art. The seed can be tempered by spraying the seed with water to raise the moisture to, for example, 8.5%. The tempered seed can be flaked using smooth roller with, for example, a gap setting of 0.23 to 0.27 mm. Heat may be applied to the flakes to deactivate enzymes, facilitate further cell rupturing, coalesce the oil droplets, or agglomerate protein particles in order to ease the extraction process. Typically, oil is removed from the heated canola flakes by a screw press to press out a major fraction of the oil from the flakes. The resulting press cake contains some residual oil.

Crude oil produced from the pressing operation typically is passed through a settling tank with a slotted wire drainage top to remove the solids expressed out with the oil in the screw pressing operation. The clarified oil can be passed through a plate and frame filter to remove the remaining fine solid particles. Canola press cake produced from the screw pressing operation can be extracted with commercial n-Hexane. The canola oil recovered from the extraction process is combined with the clarified oil from the screw pressing operation, resulting in a blended crude oil.

Free fatty acids and gums typically are removed from the crude oil by heating in a batch refining tank to which food grade phosphoric acid has been added. The acid serves to convert the non-hydratable phosphatides to a hydratable form, and to chelate minor metals that are present in the crude oil. The phosphatides and the metal salts are removed from the oil along with the soapstock. The oil-acid mixture is treated with sodium hydroxide solution to neutralize the free fatty acids and the phosphoric acid in the acid-oil mixture. The neutralized free fatty acids, phosphatides, etc. (soapstock) are drained off from the neutralized oil. A water wash may be done to further reduce the soap content of the oil. The oil may be bleached and deodorized before use, if desired, by techniques known in the art.

TAG composition of the oil can be determined using reverse phase liquid chromatography (RP LC) coupled to an evaporative light scattering detector (ELSD). In general, two C18 stationary phase LC columns can be used in series, with a gradient mobile phase of acetonitrile and methylene chloride. Individual TAGs can be identified by comparison with external or internal standards and can be quantified using a non-linear quadratic fit curve. TAG composition also can be reported based on area percent.

Oils obtained from hybrid *Brassica* varieties can have increased oxidative stability, which can be measured using, for example, an Oxidative Stability Index Instrument (e.g., from Omnion, Inc., Rockland, Mass.) according to AOCS Official Method Cd 12b-92 (revised 1993). Oxidative stability is often expressed in terms of "AOM" hours. Oxidative stability further can be increased by addition of one of more antioxidants. For example, zinc dithiophosphates, methyl dithiocarbamates, hindered phenols, phenol sulfides, metal phenol sulfides, metal salicylates, aromatic amines, phosphosulfurized fats and olefins, sulfurized olefins, sulfurized fats and fat derivatives, sulfurized paraffins, sulfurized carboxylic acids, disalieylal-1,2,-propane diamine, 2,4-bis(alkyldithio-1,3,4-thiadiazoles), dilauryl selenide, or combinations thereof, can be used to increase oxidative stability. Antioxidants are typically present in amounts ranging from 0.001% to about 5%, based on the weight of the composition.

Oils can be formulated for industrial applications including as lubricating or slip agents by addition of one or more additives. For example, an oil of the invention can be formulated as an engine lubricant by adding antioxidants, anti-foam additives, anti-wear additives, corrosion inhibitors, dispersants, detergents, and acid neutralizers, or combinations thereof. Specific oil formulations will vary depending on the end use and can be assessed using standard techniques. Typically, additives are present in amounts totaling from about 0.01% to about 20% based on the weight of the composition.

Anti-wear additives adsorb on metal and provide a film that reduces metal-to-metal contact. In general, anti-wear additives include zinc dialkyldithiophosphates, tricresyl phosphate, didodecyl phosphite, sulfurized sperm oil, sulfurized terpenes, and zinc dialkyldithiocarbamate, and are used in amounts from about 0.05% to about 4.5%.

Corrosion inhibitors include dithiophosphates and in particular, zinc dithiophosphates, metal sulfonates, metal phenate sulfides, fatty acids, acid phosphate esters, and alkyl succinic acids.

Anti-foam additives reduce or prevent the formation of a stable surface foam and are typically present in amounts from about 0.00003% to about 0.05%. Polymethylsiloxanes, polymethacrylates, salts of alkylene dithiophosphates, amyl acrylate telomer, and poly (2-ethylhexylacrylate-co-ethyl acrylate) are non-limiting examples of anti-foam additives.

Detergents and dispersants are polar materials that provide a cleaning function. Detergents include metal sulfonates, metal salicylates, and metal thiophosphonates. Dispersants include polyamine succinimides, hydroxy benzyl polyamines, polyamine succinamides, polyhydroxy succinic esters, and polyamine amide imadazolines.

Food Compositions

The invention also features food compositions containing the oils described above. For example, oils having a low linolenic acid content (<6%) in combination with a low (60-70%), mid (70-80%), or high (>80%) oleic acid content can be used to replace or reduce the amount of hydrogenated oils (e.g., partially hydrogenated oils) in various food products such that the level of trans fatty acids is reduced in the food products. In particular, canola oils having a mid or high oleic acid content in combination with a low linolenic acid content can be used to replace or reduce the amount of partially hydrogenated oils in processed or packaged food products, including bakery products such as cookies, muffins, doughnuts, pastries (e.g., toaster pastries), pie fillings, pie crusts, pizza crusts, frostings, breads, biscuits, and cakes, breakfast cereals, breakfast bars, puddings, and crackers.

For example, an oil of the invention can be used to produce sandwich cookies that contain no or reduced levels of partially hydrogenated oils in the cookie and/or crème filling. Such a cookie composition can include, for example, in addition to canola oil, flour, sweetener (e.g., sugar, molasses, honey, high fructose corn syrup, artificial sweetener such as sucralose, saccharine, aspartame, or acesulfame potassium, and combinations thereof), eggs, salt, flavorants (e.g., chocolate, vanilla, or lemon), a leavening agent (e.g., sodium bicarbonate or other baking acid such as monocalcium phosphate monohydrate, sodium aluminum sulfate, sodium acid pyrophosphate, sodium aluminum phosphate, dicalcium phosphate, glucano-deltalactone, or potassium hydrogen tartrate, or combinations thereof), and optionally, an emulsifier (e.g., mono- and diglycerides of fatty acids, propylene glycol mono- and di-esters of fatty acids, glycerol-lactose esters of fatty acids, ethoxylated or succinylated mono- and diglycerides, lecithin, diacetyl tartaric acid esters or mono- and diglycerides, sucrose esters of glycerol, and combinations thereof). A crème filling composition can include, in addition to canola oil, sweetener (e.g., powdered sugar, granulated sugar, honey, high fructose corn syrup, artificial sweetener, or combinations thereof), flavorant (e.g., vanilla, chocolate, or lemon), salt, and, optionally, emulsifier.

Canola oils (e.g., with a low oleic acid and low linolenic acid content) also are useful for frying applications due to the polyunsaturated content, which is low enough to have improved oxidative stability for frying yet high enough to impart the desired fried flavor to the food being fried. For example, canola oils can be used to produce fried foods such as snack chips (e.g., corn or potato chips), French fries, or other fast foods.

Oils of the invention also can be used to formulate spray coatings for food products (e.g., cereals or snacks such as crackers). In some embodiments, the spray coating can include other vegetable oils such as sunflower, cottonseed, corn, or soybean oils. A spray coating also can include an antioxidant and/or a seasoning.

The invention will be further described in the following examples, which do not limit the scope of the invention described in the claims.

EXAMPLES

Example 1

Production of Hybrid Canola Varieties with a C18:1 Content from 60%-74% and C18:3 Content Less than 4%

Hybrid canola varieties yielding seeds having an oleic acid content of 60-74% and an α-linolenic acid content of less than 4% were produced using two different female parents. One of the female parents, 98OA-308, contained CMS of the Ogura type and the mutation from IMC01 that confers a low linolenic acid phenotype. The maintainer (B) line for 98OA-308 was QT.2.024. QT.2.024 is identical to 98OA-308, except that the cytoplasm is not male sterile. The other female parent, 98OA-061, contained Ogura CMS, the mutation from IMC01 conferring a low linolenic acid phenotype, and the fad2 mutation from IMC129 that confers a mid-oleic acid phenotype. The maintainer line for 98OA-061 was 95CB501. A line designated 99KR02 was used as the male parent in crosses with 98OA-308 and 98OA-061. Line 99KR02 contains a Kosena-type fertility restorer gene and the mutation from IMC01 that confers a low linolenic acid phenotype.

The fatty acid content of seed of the parent lines and hybrid progeny is shown in Table 1. The fatty acid contents reported in all of the Tables below are based on bulk seed analysis by GC or NIR. Oleic acid is designated C18:1, linoleic acid is designated C18:2, and α-linolenic acid is designated C18:3 in all of the tables below unless otherwise noted.

$F_1$ hybrid seed (designated 1HKP5R01, also called CNH501R) harvested from the female plants in Example 1A had a C18:1 content of about 67.03% and a C18:3 content of 2.2% (see Example 1A of Table 1). $F_1$ hybrid seed (designated 1HKA5S08) harvested from the female plants in Example 1B had a C18:1 content of about 73.47% and a C18:3 content of 1.92%. The $F_1$ hybrid seeds were planted and $F_2$ seeds were harvested from field plots of resulting plants. In Example 1A, $F_2$ hybrid seeds had a C18:1 content that ranged from 60.37% to 68.04% and a C18:3 content that ranged from 2.4% to 4.5% (see Example 1A of Table 1). For samples analyzed by GC, the average C18:1 content was 64.54±1.70%; average C18:2 content was 22.88±1.63%; and average C18:3 content was 3.15±0.52%. In Example 1B, the $F_2$ seed of 1HA5S08 had a C18:1 content of 73.35%, a C18:2 content of 15.65%, and a C18:3 content of 3.02% (see Example 1B of Table 1).

Four additional $F_1$ hybrids were produced using similar female and male parents (see "other examples" in Table 1). When 98OA-290 was used as the female parent and 99KR02 was used as the male parent, $F_1$ seeds (designated 1HKP5R03) were obtained that had a C18:1 content of 67.22%, a C18:2 content of 20.79%, and a C18:3 content of 2.10%. $F_1$ 1HKP5R03 seeds were planted and $F_2$ seeds were harvested from the resulting plants. The $F_2$ seed had a C18:1 content of 67.92%, a C18:2 content of 21.11%, and a C18:3 content of 3.55% (see "other examples" of Table 1).

When 98OA-008 was used as the female parent and 99KR01RR was used as the male parent, $F_1$ seeds (designated 1 HKA6R05) were obtained that had a C18:1 content of 68.86%, a C18:2 content of 19.47%, and a C18:3 content of 2.55%. $F_1$ 1HKA6R05 seeds were planted and $F_2$ seeds were harvested from the resulting plants. The $F_2$ seed had an average C18:1 content of 67.17±1.15%, an average C18:2 content of 20.67±0.82%, and an average C18:3 content of 3.46±0.13% (see "other examples" of Table 1).

When 98OA-021 was used as the female parent and 99KR01RR was used as the male parent, $F_1$ seeds (designated 1HKA6R07) were obtained that had a C18:1 content of 72.00%, a C18:2 content of 15.30%, and a C18:3 content of 2.58%. $F_1$ 1HKA6R07 seeds were planted and $F_2$ seeds were harvested from the resulting plants. The $F_2$ seed had an average C18:1 content of 69.69±0.46%, an average C18:2 content of 17.99±0.36%, and an average C18:3 content of 3.62±0.23% (see "other examples" of Table 1).

Overall, the $F_1$ hybrid seed from the four additional hybrids had an average C18:1 content of 69.49±2.0%, an average C18:2 content of 18.65±2.35%; and an average C18:3 content of 2.40±0.22%. The $F_2$ seeds from the four hybrids had all average C18:1 content of 68.03±1.42%, an average C18:2 content of 20.01±1.53%, and an average C18:3 content of 3.39±0.31%.

Seed yield of hybrids was 10-20% higher than open-pollinated varieties.

| | Yield Results (% vs. Q2 and 46A65), year 2 | | |
|---|---|---|---|
| | Short Season Zone (4 sites) | Mid. Season Zone (4 sites) | Long Season (6 sites) |
| CNH501R | 114.2 | 113.7 | 106.7 |
| 46A65 | 100.3 | 104.9 | 98.9 |
| Q2 | 99.7 | 95.2 | 101.1 |
| Lolinda (Low linolenic) | 89.7 | 86.4 | 85.3 |

| | Yield Results (% vs. Q2 and 46A65), year one | | |
|---|---|---|---|
| | Short Season Zone (2 sites) | Mid. Season Zone (8 sites) | Long Season (3 sites) |
| CNH501R | 117 | 109 | 104 |
| 46A65 | 99.6 | 96.3 | 101.2 |
| Q2 | 100.4 | 103.7 | 98.8 |
| Apollo (low linolenic) | 67 | 72.1 | 76.15 |

| | Estimated Parental Line Yield (% vs. Q2 and 46A65) | | |
|---|---|---|---|
| | Short Season Zone | Mid. Season Zone | Long Season |
| Mean of the Parental lines | 94 | 92 | 91 |
| RF line | 96 | 98 | 96 |
| B line for CMS | 90 | 85 | 85 |

TABLE 1

| Identifier | C160 | C180 | C181 | C182 | C183 | Total Poly | C221 | Hybrid | B_Lines |
|---|---|---|---|---|---|---|---|---|---|
| EXAMPLE 1A Parental Lines | | | | | | | | | |
| CMS lines 98OA-308 | 3.73 | 1.26 | 60.09 | 28.68 | 3.16 | 31.84 | 0.00 | 1HKP5R01 | QT.2.024 |
| RF Lines 99KR02 | 3.45 | 1.88 | 69.86 | 18.72 | 1.97 | 20.69 | 0.00 | 1HKP5R01 | |
| F1 Hybrids | | | | | | | | | |
| 1HKP5R01 | 3.91 | 1.74 | 67.03 | 22.04 | 2.20 | 24.24 | 0.03 | | |
| F2 Harvested from F1 Hybrids | | | | | | | | | |
| 1HKP5R01 | | | 68.04* | 20.64 | 3.06 | 23.70 | | | |
| CNH501R.AT | 4.32 | 1.48 | 60.37 | 27.28 | 3.20 | 30.48 | 0.03 | | |
| CNH501R.AT | 4.06 | 1.71 | 63.63 | 23.97 | 3.20 | 27.17 | 0.02 | | |
| CNH501R.BH | 4.23 | 1.55 | 65.65 | 22.03 | 3.11 | 25.14 | 0.03 | | |
| CNH501R.BH | 4.39 | 1.65 | 65.96 | 21.96 | 2.76 | 24.72 | 0.00 | | |
| CNH501R.CM | 4.25 | 1.81 | 62.18 | 24.91 | 3.04 | 27.95 | 0.05 | | |
| CNH501R.CM | 4.53 | 1.56 | 62.32 | 24.16 | 3.98 | 28.14 | 0.04 | | |
| CNH501R.CM | 3.85 | 1.79 | 64.50 | 22.26 | 3.98 | 26.24 | 0.03 | | |
| CNH501R.EC | 4.43 | 1.66 | 67.38 | 19.43 | 3.70 | 23.13 | 0.04 | | |
| CNH501R.EC | 4.34 | 1.68 | 61.89 | 25.83 | 2.66 | 28.49 | 0.05 | | |
| CNH501R.MD | 4.46 | 1.95 | 63.61 | 24.22 | 2.50 | 26.72 | 0.03 | | |
| CNH501R.MD | 4.80 | 1.76 | 64.63 | 23.09 | 2.53 | 25.62 | 0.04 | | |
| CNH501R.MD | 4.18 | 1.98 | 65.72 | 22.32 | 2.41 | 24.73 | 0.04 | | |
| CNH501R.MD | 4.38 | 2.17 | 63.43 | 23.73 | 2.61 | 26.34 | 0.04 | | |
| CNH501R.NP | 4.13 | 1.76 | 63.74 | 22.57 | 4.55 | 27.12 | 0.03 | | |
| CNH501R.NP | 4.39 | 1.55 | 66.46 | 20.98 | 3.41 | 24.39 | 0.03 | | |
| CNH501R.NP | 4.45 | 1.60 | 65.14 | 22.57 | 2.90 | 25.47 | 0.03 | | |
| CNH501R.OK | 4.46 | 1.55 | 65.35 | 22.12 | 3.22 | 25.34 | 0.03 | | |
| CNH501R.OK | 4.27 | 1.54 | 66.44 | 21.62 | 2.89 | 24.51 | 0.03 | | |
| CNH501R.WT | 4.13 | 1.57 | 66.04 | 21.88 | 3.13 | 25.01 | 0.02 | | |
| CNH501R.WT | 4.16 | 1.50 | 65.43 | 22.07 | 3.44 | 25.51 | 0.03 | | |
| CNH501R.WT | 4.20 | 1.46 | 65.63 | 22.18 | 3.16 | 25.34 | 0.05 | | |
| CNH501R.WY | 4.36 | 2.08 | 63.32 | 23.34 | 3.51 | 26.85 | 0.04 | | |
| CNH501R.WY | 4.38 | 1.69 | 65.61 | 22.07 | 2.79 | 24.86 | 0.02 | | |
| CNH501R.WY | 4.11 | 1.97 | 64.56 | 22.64 | 2.96 | 25.60 | 0.03 | | |
| MEAN | 4.30 | 1.71 | 64.54 | 22.88 | 3.15 | 26.03 | 0.03 | | |

TABLE 1-continued

| Identifier | C160 | C180 | C181 | C182 | C183 | Total Poly | C221 | Hybrid | B_Lines |
|---|---|---|---|---|---|---|---|---|---|
| EXAMPLE 1B Parental Lines ||||||||||
| CMS lines 98OA-061 | 3.36 | 1.59 | 73.30 | 14.40 | 3.26 | 17.66 | 0.15 | 1HKA5S08 | 95CB501 |
| RF lines 99KR02 | 3.91 | 1.73 | 68.08 | 20.87 | 2.10 | 22.97 | 0.00 | 1HKA5S08 | |
| F1 Hybrids ||||||||||
| 1HKA5S08 | 3.51 | 2.36 | 73.47 | 14.74 | 1.92 | 16.66 | 0.04 | | |
| F2 Harvested from F1 Hybrids ||||||||||
| 1HKA5S08 | | | 73.35* | 15.65 | 3.02 | 18.67 | | | |
| OTHER EXAMPLES CMS Lines ||||||||||
| 98OA-290 | 4.12 | 1.47 | 60.52 | 27.18 | 3.21 | 30.39 | 0.05 | 1HKP5R03 | QT.2.056 |
| 98OA-021 | 3.49 | 1.64 | 74.48 | 13.40 | 3.15 | 16.55 | 0.06 | 1HKA6R07 | 93KN.1090 |
| 98KA-008 | 3.58 | 1.59 | 62.01 | 26.36 | 2.99 | 29.35 | 0.00 | 1HKA6R05 | 92FR.0206 |
| Restorer Lines ||||||||||
| 99KR02 | 3.80 | 1.64 | 67.47 | 21.66 | 2.32 | 23.98 | 0.00 | 1HKP5R03 | |
| 99KR01RR | 3.44 | 1.77 | 65.98 | 21.64 | 3.74 | 25.38 | 0.03 | 1HKA6R07 | |
| 99KR01RR | 3.45 | 1.74 | 68.16 | 20.13 | 3.36 | 23.49 | 0.04 | 1HKA6R05 | |
| F1 Hybrids ||||||||||
| 1HKP5R03 | 4.05 | 2.02 | 67.22 | 20.79 | 2.10 | 22.89 | 0.22 | | |
| 1HKA6R05 | 3.74 | 1.36 | 68.86 | 19.47 | 2.55 | 22.02 | 0.15 | | |
| 1HKA6R07 | 3.87 | 2.34 | 72.00 | 15.30 | 2.58 | 17.88 | 0.06 | | |
| F2 Harvested from F1 Hybrids ||||||||||
| 1HKP5R03 | | | 67.92* | 21.11 | 3.55 | 24.66 | | | |
| 1HKA6R05 | | | 67.90* | 20.87 | 3.33 | 24.20 | | | |
| 1HKA6R05 | | | 65.85* | 21.37 | 3.46 | 24.83 | | | |
| 1HKA6R05 | | | 67.77* | 19.76 | 3.60 | 23.36 | | | |
| 1HKA6R07 | | | 69.29* | 18.28 | 3.45 | 21.73 | | | |
| 1HKA6R07 | | | 69.60* | 17.59 | 3.84 | 21.43 | | | |
| 1HKA6R07 | | | 70.19* | 18.12 | 3.57 | 21.69 | | | |

A "*" indicates that the fatty acid composition of this hybrid was determined by NIR. Fatty acid composition in all other samples was determined by GC.

Example 2

Production of Hybrid Canola Varieties with a C18:1 Content from 71%-80% and C18:3 Content of Less than 4%

Hybrid canola varieties yielding seeds having a C18:1 content of 71-80% and a C18:3 content of less than 4% were produced using parents having a mutation in a fad2 gene and the mutation from IMC01 that confers a low linolenic acid phenotype. The seed yield of such hybrid canola varieties will be 10-20% higher than available open-pollinated varieties.

In Example 2A, the female parent, 98OA-261, contained Ogura CMS, the mutation from IMC01 that confers a low linolenic acid phenotype, and one of the fad2 mutations from Q4275 that confer a mid-oleic acid phenotype. 98OA-261 was maintained using 95ZX503 as the B-line. The male or pollen parent, GA-I-097-13-04, contained a Kosena fertility restorer gene, the mutation from IMC01 that confers a low linolenic acid phenotype, and one of the fad2 mutations from Q4275 that confers a higher oleic acid phenotype.

The fatty acid content of seed of the parent lines and hybrid progeny is shown in Example A2 of Table 2. The oleic acid content in seeds from each of the parent lines was about 60 to 70%. $F_1$ hybrid seed harvested from the female plant had a C18:1 content of about 77.58%, a C18:2 content of 10.12%, and a C18:3 content of 2.6%. $F_1$ hybrid seeds were planted and $F_2$ seeds were harvested from field plots of the resulting plants. The $F_2$ hybrid seeds had a C18:1 content of 75.48%, a C18:2 content of 13.08%, and a C18:3 content of 3.88% (see Example 2A of Table 2).

In Example 2B, the female parent, 98OA-064, contained Ogura CMS, the mutation from IMC01 conferring a low linolenic acid phenotype, and the fad2 mutation from IMC129 that confers a mid-oleic acid phenotype. 98OA-064 was maintained using 95CB505 as the B-line. The male parent, GA-I-097-13-02, contained a Kosena fertility restorer gene, the mutation from IMC01 that confers a low linolenic acid phenotype, and one of the fad2 mutations from Q4275 that confers a higher oleic acid phenotype. See Example 2B of Table 2 for the fatty acid content of the parent lines and hybrid progeny. As shown in Example 2B of Table 2, $F_1$ hybrid seed (01GHYB487505) harvested from the female plant had a C18:1 content of about 77.84%, a C18:2 content of 9.08%, and a C18:3 content of 2.32%. $F_1$ hybrid seeds were planted and $F_2$ seeds were harvested from field plots of the resulting plants. The $F_2$ hybrid seeds had a C18:1 content of 79.01%, a C18:2 content of 9.52%, and a C18:3 content of 3.59%.

Additional $F_1$ hybrids were produced using similar female and male parents (see "other examples in Table 2). When 98OA-062 was used as the female parent and GA-I-097-13-10 was used as the male parent, $F_1$ seeds (designated 01GHYB7503) were obtained that had a C18:1 content of 79.10%, a C18:2 content of 8.60%, and a C18:3 content of 2.49%. $F_1$ 01GHYB7503 seeds were planted and $F_2$ 01GHYB7503 seeds were harvested from the resulting plants. The $F_2$ 01GHYB7503 seed had a C18:1 content of 79.83%, a C18:2 content of 9.69%, and a C18:3 content of 2.89%. When 905.3 was used as the female parent and GA-I-096-81-07 was used as the male parent, $F_1$ seeds (designated 01GHYB7514) were obtained that had a C18:1 content of 75.44%, a C18:2 content of 12.57%, and a C18:3 content of 2.00%. $F_1$ 01GHYB7514 seeds were planted and $F_2$ 01GHYB7514 seeds were harvested from the resulting plants. The $F_2$ 01GHYB7514 seed had a C18:1 content of 77.33%, a C18:2 content of 11.30%, and a C18:3 content of 3.62%. See "Other Examples" of Table 2 for the fatty acid content of each hybrid.

content of 13.14%, and a C18:3 content of 2.16% (see Example 3A of Table 3). $F_1$ 02HA0113 hybrid seeds were planted and $F_2$ seeds were harvested from field plots of the resulting plants. The $F_2$ hybrid seeds had a C18:1 content of 76.42%, a C18:2 content of 12.40%, and a C18:3 content of 2.53%.

TABLE 2

|  | Identifier | C160 | C180 | C181 | C182 | C183 | Total Poly | C221 | Hybrid | B_Lines |
|---|---|---|---|---|---|---|---|---|---|---|
| | | | | EXAMPLE 2A | | | | | | |
| | | | | Parental Lines | | | | | | |
| CMS Lines | 98OA-261 | 2.82 | 1.36 | 76.93 | 12.42 | 2.99 | 15.41 | 0.04 | 01GHYB7502 | 95ZX503 |
| RF lines | GA-I-097-13-04 | 3.84 | 2.62 | 79.83 | 6.64 | 2.50 | 9.14 | 0.02 | 01GHYB 7502 | |
| | | | | F1 Hybrids | | | | | | |
| | 01GHYB7502 | 3.47 | 2.44 | 77.58 | 10.12 | 2.60 | 12.72 | 0.00 | | |
| | | | | F2 Harvested from F1 Hybrids | | | | | | |
| | 01GHYB7502 | | | 75.48* | 13.08 | 3.88 | 16.96 | | | |
| | | | | EXAMPLE 2B | | | | | | |
| | | | | Parental Lines | | | | | | |
| CMS lines | 98OA-064 | 2.86 | 1.64 | 76.26 | 10.84 | 3.39 | 14.23 | 0.07 | 01GHYB 7505 | 95CB505 |
| RF lines | GA-I-097-13-02 | 3.75 | 2.56 | 79.51 | 6.88 | 2.84 | 9.72 | 0.02 | 01GHYB 7505 | |
| | | | | F1 Hybrids | | | | | | |
| | 01GHYB7505 | 3.42 | 2.63 | 77.84 | 9.08 | 2.32 | 11.40 | 0.03 | | |
| | | | | F2 Harvested from F1 Hybrids | | | | | | |
| | 01GHYB7505 | | | 79.01* | 9.52 | 3.59 | 13.11 | | | |
| | | | | OTHER EXAMPLES | | | | | | |
| | | | | Parental Lines | | | | | | |
| CMS lines | 905.3 | 3.23 | 1.67 | 75.48 | 13.10 | 2.83 | 15.93 | 0.08 | 01GHYB 7514 | 93KN-1027 |
| | 98OA-062 | 3.18 | 1.62 | 76.87 | 11.02 | 3.11 | 14.13 | 0.06 | 01GHYB 7503 | 95CB504 |
| RF lines | GA-I-097-13-10 | 3.64 | 2.13 | 80.96 | 6.65 | 2.70 | 9.35 | 0.00 | 01GHYB7503 | |
| | GA-I-096-81-07 | 3.23 | 1.67 | 75.48 | 13.10 | 2.83 | 15.93 | 0.08 | 01GHYB7514 | |
| | | | | F1 Hybrids | | | | | | |
| | 01GHYB7503 | 3.32 | 2.57 | 79.10 | 8.60 | 2.49 | 11.09 | 0.00 | | |
| | 01GHYB7514 | 3.92 | 2.29 | 75.44 | 12.57 | 2.00 | 14.57 | 0.03 | | |
| | | | | F2 Harvested from F1 Hybrids | | | | | | |
| | 01GHYB7503 | | | 79.83* | 9.69 | 2.89 | 12.58 | | | |
| | 01GHYB7514 | | | 77.33* | 11.30 | 3.62 | 14.92 | | | |

A "*" indicates that the fatty acid composition of this hybrid was determined by NIR. Fatty acid composition in all other samples was determined by GC.

Example 3

Production of Hybrid Canola Varieties with a C18:1 Content from 71%-80% and C18:3 Content of Less than 4%

Hybrid canola varieties yielding seeds having a C18:1 content of 71-80% and a C18:3 content of less than 4% were produced using parents having a mutation in a fad2 gene and the mutation from IMC01 that confers a low linolenic acid phenotype. The seed yield of such hybrid canola varieties will be 10-20% higher than available open-pollinated varieties.

In Example 3A, the female parent, 99RR-153, contained Ogura CMS and the mutation from IMC01 that confers a low linolenic acid phenotype. 99RR-153 was maintained using 95RTC0701 as the B-line. The male parent, 00KR08.19-01, contained a Kosena fertility restorer gene, the mutation from IMC01 that confers a low linolenic acid phenotype, and both fad2 mutations from Q4275 that confer a high oleic acid phenotype. The fatty acid content of seed produced by these parent lines and hybrid progeny is shown in Example 3A of Table 3.

$F_1$ hybrid seed (designated 02HA0113) harvested from the female plant had a C18:1 content of about 76.43%, a C18:2

In Example 3B, the female parent, 99RR-183, contained Ogura CMS, the mutation from IMC01 conferring a low linolenic acid phenotype, and the fad2 mutation from IMC129 that confers a mid-oleic acid phenotype. 99RR-183 was maintained using 95RTC1042 as the B-line. The male parent, 00KR08.19-01, contained a Kosena fertility restorer gene, the mutation from IMC01 that confers a low linolenic acid phenotype, and both fad2 mutations from Q4275 that confers a higher oleic acid phenotype. The fatty acid content of seed produced by these parent lines and hybrid progeny is shown in Example 3B of Table 3.

$F_1$ hybrid seed, designated 02HP0115, harvested from the female plant had a C18:1 content of about 78.19%, a C18:2 content of 10.76%, and a C18:3 content of 2.59% (see Example 3B of Table 3). $F_1$ 02HP0115 hybrid seeds were planted and $F_2$ seeds were harvested from field plots of the resulting plants. The $F_2$ hybrid seeds had a C18:1 content of 78.03%, a C18:2 content of 10.46%, and a C18:3 content of 3.22%.

TABLE 3

|  | Identifier | C160 | C180 | C181 | C182 | C183 | Total Poly | C221 | Hybrid | B_Lines |
|---|---|---|---|---|---|---|---|---|---|---|
|  |  |  |  | EXAMPLE 3A Parental Lines |  |  |  |  |  |  |
| CMS lines | 99RR-153 | 3.90 | 2.83 | 66.34 | 20.42 | 2.33 | 22.75 | 0.02 | 02HA0113 | 95RTC0701 |
| RF lines | 00KR08.19-01 | 3.05 | 1.51 | 86.38 | 3.86 | 2.08 | 5.94 | 0.03 | 02HA0113 |  |
|  |  |  |  | F1 Hybrids |  |  |  |  |  |  |
|  | 02HA0113 | 3.52 | 1.33 | 76.43 | 13.14 | 2.16 | 15.30 | 0.00 |  |  |
|  |  |  |  | F2 Harvested from F1 Hybrids |  |  |  |  |  |  |
|  | 02HA0113 | 3.23 | 2.10 | 76.42 | 12.40 | 2.53 | 14.93 | 0.02 |  |  |
|  |  |  |  | EXAMPLE 3B Parental Lines |  |  |  |  |  |  |
| CMS lines | 99RR-183 | 3.26 | 2.39 | 74.15 | 12.89 | 2.42 | 15.31 | 0.05 | 02HP0115 | 95RTC1042 |
| RF lines | 00KR08.19-01 | 3.11 | 1.59 | 84.99 | 4.49 | 2.30 | 6.79 | 0.03 | 02HP0115 |  |
|  |  |  |  | F1 Hybrids |  |  |  |  |  |  |
|  | 02HP0115 | 3.13 | 2.00 | 78.19 | 10.76 | 2.59 | 13.35 | 0.00 |  |  |
|  |  |  |  | F2 Harvested from F1 Hybrids |  |  |  |  |  |  |
|  | 02HP0115 | 3.79 | 1.70 | 78.03 | 10.46 | 3.22 | 13.68 | 0.03 |  |  |

Example 4

Production of Hybrid Canola Varieties with a C18:1 Content from 71%-80% and C18:3 Content of Less than 4%

Hybrid canola varieties yielding seeds having a C18:1 content of 71-80% and a C18:3 content of less than 4% were produced using parents having a mutation in a fad2 gene and the mutation from IMC01 that confers a low linolenic acid phenotype. The seed yield of such hybrid canola varieties will be 10-20% higher than available open-pollinated varieties.

In Example 4A, the female parent, 98OA-195, contained Ogura CMS, the mutation from IMC01 that confers a low linolenic acid phenotype, and both fad2 mutations from Q4275. 98OA-195 was maintained using 95YM501 as the B-line. The male parent was 99KR02 (see Example 1A and Table 1 for a description of 99KR02). The fatty acid content of seed of these parent lines and hybrid progeny is shown in Example 4A in Table 4.

$F_1$ hybrid seed (designated 01HKA5S14) harvested from the female plant had an average C18:1 content of 76.95%±0.29%, an average C18:2 content of 11.93%±0.20%, and an average C18:3 content of 1.98%±0.08%, based on bulk seed analysis of three different plots of 01HKA5S14 seeds (see Table 4). $F_1$ hybrid seeds were planted and $F_2$ 01HKA5S14 seeds were harvested from field plots of the resulting plants. The $F_2$ hybrid seeds had an average C18:1 content of 76.05%±0.83%, an average C18:2 content of 12.90%±0.79%, and an average C18:3 content of 2.96%±0.08%, based on bulk seed analysis of three different plots of 01HKA5S14 seeds. See Example 4A in Table 4 for the fatty acid content of each plot of 01HKA5S14 seeds.

In Example 4B, the female parent, 98OA-226, contained Ogura CMS, the mutation from IMC01 conferring a low linolenic acid phenotype, and both fad2 mutations from Q4275. 98OA-226 was maintained using 95YY501 as the B-line. The male parent, 99KR01RR, contained a Kosena fertility restorer gene and the mutation from IMC01 that confers a low linolenic acid phenotype. The fatty acid content of seed of these parent lines and hybrid progeny is shown in Example 4B of Table 4.

$F_1$ hybrid seed, designated 1HKA6R17, harvested from the female plant had an average C18:1 content of 77.24%±0.40%, an average C18:2 content of 11.09%±0.33%, and an average C18:3 content of 2.29%±0.11%, based on bulk seed analysis of three different plots of 1HKA6R17 seeds (see Example 4B of Table 4). $F_1$ 1HKA6R17 hybrid seeds were planted and $F_2$ 1HKA6R17 seeds were harvested from field plots of the resulting plants. The $F_2$ hybrid seeds had a C18:1 content of 76.17%, a C18:2 content of 12.72%, and a C18:3 content of 3.01%. See Example 4B of Table 4.

Additional $F_1$ hybrids were produced using similar female and male parents (see "other examples in Table 4"). When 98OA-175 was used as the female parent and 99KR02 was used as the male parent, $F_1$ seeds (designated 1HKP5S35) were obtained that had a C18:1 content of 76.86%, a C18:2 content of 11.61%, and a C18:3 content of 2.07%. $F_1$ 1HKP5S35 seeds were planted and $F_2$ 01HKP5S35 seeds were harvested from the resulting plants. The $F_2$ seed had a C18:1 content of 75.88%, a C18:2 content of 12.99%, and a C18:3 content of 2.68%. When 98OA-175 was used as the female parent and 99KR01RR was used as the male parent, $F_1$ seeds (designated 1HKP5S33) were obtained that had a C18:1 content of about 76.56%, a C18:2 content of 11.73-12.21%, and a C18:3 content of 2.53-2.59%. $F_1$ 1HKP5S33 seeds were planted and $F_2$ seeds were harvested from the resulting plants. The $F_2$ seed had a C18:1 content of 76.14%, a C18:2 content of 12.97%, and a C18:3 content of 3.22%. See "Other Examples" of Table 4 for the fatty acid content of each hybrid.

TABLE 4

| | Identifier | C160 | C180 | C181 | C182 | C183 | Total Poly | C221 | Hybrid | B_Lines |
|---|---|---|---|---|---|---|---|---|---|---|
| | | | | EXAMPLE 4A Parental Lines | | | | | | |
| CMS lines | 98OA-195 | 2.81 | 1.75 | 84.29 | 4.70 | 2.27 | 6.97 | 0.06 | 1HKA5S14 | 95YM501 |
| RF lines | 99KR02 | 3.80 | 1.64 | 67.47 | 21.66 | 2.32 | 23.98 | 0.00 | 1HKA5S14 | |
| | | | | F1 Hybrids | | | | | | |
| | 1HKA5S14 | 3.28 | 2.37 | 76.85 | 11.75 | 1.89 | 13.64 | 0.04 | | |
| | 1HKA5S14 | 3.34 | 2.08 | 77.28 | 12.14 | 2.04 | 14.18 | 0.03 | | |
| | 1HKA5S14 | 3.54 | 2.47 | 76.73 | 11.89 | 2.01 | 13.90 | 0.03 | | |
| | | | | F2 Harvested from F1 Hybrids | | | | | | |
| | 1HKA5S14 | | | 75.82* | 13.34 | 2.90 | 16.24 | | | |
| | 1HKA5S14 | | | 75.36* | 13.38 | 2.92 | 16.30 | | | |
| | 1HKA5S14 | | | 76.97* | 11.98 | 3.05 | 15.03 | | | |
| | | | | EXAMPLE 4B Parental Lines | | | | | | |
| CMS lines | 98OA-226 | 2.61 | 1.64 | 85.10 | 4.82 | 2.29 | 7.11 | 0.00 | 1HKA6R17 | 95YY501 |
| RF lines | 99KR01RR | 3.44 | 1.77 | 65.98 | 21.64 | 3.74 | 25.38 | 0.03 | 1HKA6R17 | |
| | | | | F1 Hybrids | | | | | | |
| | 1HKA6R17 | 3.41 | 2.60 | 76.87 | 10.73 | 2.27 | 13.00 | 0.08 | | |
| | 1HKA6R17 | 3.13 | 2.22 | 77.67 | 11.37 | 2.41 | 13.78 | 0.04 | | |
| | 1HKA6R17 | 3.49 | 1.33 | 77.19 | 11.18 | 2.19 | 13.37 | 0.22 | | |
| | | | | F2 Harvested from F1 Hybrids | | | | | | |
| | 1HKA6R17 | | | 76.17* | 12.72 | 3.01 | 15.73 | | | |
| | | | | OTHER EXAMPLES Parental Lines | | | | | | |
| CMS lines | 98OA-175 | 2.84 | 1.61 | 83.30 | 5.37 | 2.84 | 8.21 | 0.04 | 1HKP5S35 | 95XE503 |
| | 98OA-175 | 2.84 | 1.61 | 83.30 | 5.37 | 2.84 | 8.21 | 0.04 | 1HKP6R33 | 95XE503 |
| RF lines | 99KR02 | 3.60 | 1.68 | 67.98 | 21.17 | 2.22 | 23.39 | 0.00 | 1HKP5S35 | |
| | 99KR01RR | 3.45 | 1.74 | 68.16 | 20.13 | 3.36 | 23.49 | 0.04 | 1HKP6R33 | |
| | | | | F1 Hybrids | | | | | | |
| | 1HKP5S35 | 3.41 | 2.40 | 76.86 | 11.61 | 2.07 | 13.68 | 0.03 | | |
| | 1HKP6R33 | 3.57 | 2.08 | 76.57 | 11.73 | 2.59 | 14.32 | 0.00 | | |
| | 1HKP6R33 | 3.42 | 1.90 | 76.55 | 12.21 | 2.53 | 14.74 | 0.00 | | |
| | | | | F2 Harvested from F1 Hybrids | | | | | | |
| | 1HKP5S35 | | | 75.88* | 12.99 | 2.68 | 15.67 | | | |
| | 1HKP6R33 | | | 76.14* | 12.97 | 3.22 | 16.19 | | | |

A "*" indicates that the fatty acid composition of this hybrid was determined by NIR. Fatty acid composition in all other samples was determined by GC.

Example 5

Production of Hybrid Canola Varieties with a C18:1 Content from 71%-80% and C18:3 Content Less than 4%

Hybrid canola varieties yielding seeds having a C18:1 content of 71-80% and a C18:3 content of less than 4% were produced using parents having a mutation in a fad2 gene and the mutation from IMC01 that confers a low linolenic acid phenotype. The seed yield of such hybrid canola varieties will be 10-20% higher than available open-pollinated varieties.

In Example 5A, the female parent, 99RR-236, contained Ogura CMS and the mutation from IMC01 that confers a low linolenic acid phenotype. 99RR-236 was maintained using QT.2.024 as the B-line. The male parent, 00KR08.19-01, contained a Kosena fertility restorer gene, the mutation from IMC01 that confers a low linolenic acid phenotype, and both fad2 mutations from Q4275. The fatty acid content of seed of these parent lines and hybrid progeny is shown in Example 5A of Table 5.

$F_1$ hybrid seed (designated 02HA0104) harvested from the female plant had a C18:1 content of 72.45%, a C18:2 content of 16.07%, and a C18:3 content of 2.49% (see Example 5A of Table 5). $F_1$ hybrid seeds were planted and $F_2$ seeds were harvested from the resulting plants. The $F_2$ hybrid seeds had a C18:1 content of 74.19-75.54%, a C18:2 content of 13.06-14.54%, and a C18:3 content of 2.74-2.79%. See Example 5A of Table 5 for the fatty acid content of each plot of 00HA0104 seeds.

In Example 5B, the female parent, 99RR-259, contained Ogura CMS and the mutation from IMC01 that confers a low linolenic acid phenotype. 99RR-259 was maintained using QT.2.147 as the B-line. The male parent, 00KR08.19-01, contained a Kosena fertility restorer gene, the mutation from IMC01 that confers a low linolenic acid phenotype, and both fad2 mutations from Q4275. The fatty acid content of seed of these parent lines and hybrid progeny is shown in Example 5B of Table 5.

$F_1$ hybrid seed, designated 00HA0107, harvested from the female plant had a C18:1 content of 72.89%, a C18:2 content of 15.44%, and a C18:3 content of 3.09 (see Example 5B of Table 5). $F_1$ 02HA0107 hybrid seeds were planted and $F_2$ seeds were harvested from the resulting plants. The $F_2$ hybrid seeds had a C18:1 content of 71.82-73.59%, a C18:2 content of 14.46-15.24%, and a C18:3 content of 3.14-4.40%. See Example 5B of Table 5.

TABLE 5

| | C160 | C180 | C181 | C182 | C183 | Total Polys | C221 | Hybrid | B_Line |
|---|---|---|---|---|---|---|---|---|---|
| EXAMPLE 5A Parental Lines | | | | | | | | | |
| CMS lines 99RR-236 | 3.79 | 1.80 | 63.73 | 24.08 | 2.64 | 26.72 | 0.03 | 02HA0104 | QT.2.024 |
| RF lines 00KR08.19-01 | 3.05 | 1.51 | 86.38 | 3.86 | 2.08 | 5.94 | 0.03 | 02HA0104 | |
| F1 Hybrids | | | | | | | | | |
| 02HA0104 | 3.84 | 1.88 | 72.46 | 16.07 | 2.49 | 18.56 | 0.03 | | |
| F2 Hybrids | | | | | | | | | |
| 02HA0104-EM | 3.44 | 1.86 | 74.19 | 14.54 | 2.79 | 17.33 | 0.03 | | |
| 02HA0104-MD | 3.79 | 1.70 | 75.54 | 13.06 | 2.74 | 15.80 | 0.03 | | |
| EXAMPLE 5B Parental Lines | | | | | | | | | |
| CMS lines 99RR-259 | 4.52 | 2.16 | 62.29 | 23.15 | 3.74 | 26.89 | 0.00 | 02HA0107 | QT.2.147 |
| RF lines 00KR08.19-01 | 3.11 | 1.59 | 84.99 | 4.49 | 2.30 | 6.79 | 0.03 | 02HA0107 | |
| F1 Hybrids | | | | | | | | | |
| 02HA0107 | 4.02 | 1.12 | 72.89 | 15.44 | 3.09 | 18.53 | 0.02 | | |
| F2 Hybrids | | | | | | | | | |
| 02HA0107-CM | 3.31 | 1.88 | 71.82 | 15.24 | 4.40 | 19.64 | 0.03 | | |
| 02HA0107-MD | 3.93 | 1.75 | 73.59 | 14.46 | 3.14 | 17.60 | 0.03 | | |

Example 6

Production of Hybrid Canola Varieties with a C18:1 Content from 81%-89% and C18:3 Content Less than 4%

Hybrid canola varieties yielding seeds having a C18:1 content of 81-89% and a C18:3 content of less than 4% were produced using parents having a mutation in two different fad2 genes and the mutation from IMC01 that confers a low linolenic acid phenotype. The seed yield of such hybrid canola varieties will be 10-20% higher than the open-pollinated varieties.

In Example 6A, the female parent, 98OA-226 contained Ogura CMS, the mutation from IMC01 that confers a low linolenic acid phenotype, and both fad2 mutations from Q4275. 98OA-226 was maintained using 95YY501 as the B-line. The male parent, GA-I-097-26, contained a Kosena fertility restorer gene, the mutation from IMC01 that confers a low linolenic acid phenotype, and both fad2 mutations from Q4275. The fatty acid content of seed of the parent lines and hybrid progeny is shown in Example 6A of Table 6.

$F_1$ hybrid seed (designated 01GHYB8502) harvested from the female plant had a C18:1 content of 84.13%, a C18:2 content of 3.50%, and a C18:3 content of 2.09% (see Example 6A of Table 6). $F_1$ hybrid seeds were planted and $F_2$ seeds were harvested from the resulting plants. The $F_2$ hybrid seeds had a C18:1 content of 85.45%, a C18:2 content of 3.45%, and a C18:3 content of 3.86%.

In Example 6B, the female parent, 98OA-195, contained Ogura CMS, the mutation from IMC01 that confers a low linolenic acid phenotype, and both fad2 mutations from Q4275. 98OA-195 was maintained using 95YM501 as the B-line. The male parent, GA-I-096-93-03, contained a Kosena fertility restorer gene, the mutation from IMC01 that confers a low linolenic acid phenotype, and both fad2 mutations from Q4275. The fatty acid content of seed of the parent lines and hybrid progeny is shown in Example 6B of Table 6.

$F_1$ hybrid seed, designated 01GHYB8505, harvested from the female plant had a C18:1 content of 81.48%, a C18:2 content of 5.16%, and a C18:3 content of 2.82 (see Example 6B of Table 6). $F_1$ 01GHYB85057 hybrid seeds were planted and $F_2$ seeds were harvested from the resulting plants. The $F_2$ hybrid seeds had a C18:1 content of 84.48%, a C18:2 content of 4.27%, and a C18:3 content of 2.82%.

Additional $F_1$ hybrids were produced using similar female and male parents (see "Other Examples" in Table 6). When 98OA-252 was used as the female parent and GA-I-097-26 was used as the male parent, $F_1$ seeds (designated 01GHYB8503) were obtained that had a C18:1 content of 83.71%, a C18:2 content of 3.78%, and a C18:3 content of 2.16%. $F_1$ 01GHYB8503 seeds were planted and $F_2$ seeds were harvested from the resulting plants. The $F_2$ seed had a C18:1 content of 84.46%, a C18:2 content of 6.13%, and a C18:3 content of 1.53%. When 98OA-204 was used as the female parent and GA-I-097-93-02 was used as the male parent, $F_1$ seeds (designated 01GHYB8504) were obtained that had a C18:1 content of about 81.12%, a C18:2 content of 5.57%, and a C18:3 content of 2.61%. $F_1$ 01GHYB8504 seeds were planted and $F_2$ seeds were harvested from the resulting plants. The $F_2$ seed had a C18:1 content of 84.15%, a C18:2 content of 4.62%, and a C18:3 content of 5.16%. When 98OA-174 was used as the female parent and GA-I-097-04-02 was used as the male parent, $F_1$ seeds (designated 01GHYB8506) were obtained that had a C18:1 content of about 84.28%, a C18:2 content of 3.68%, and a C18:3 content of 2.06%. $F_1$ 01GHYB8506 seeds were planted and $F_2$ seeds were harvested from the resulting plants. The $F_2$ seed had a C18:1 content of 83.97%, a C18:2 content of 5.16%, and a C18:3 content of 3.84%. See "Other Examples" of Table 6 for the fatty acid content of each hybrid.

TABLE 6

| Identifier | C160 | C180 | C181 | C182 | C183 | Total Poly | C221 | Hybrid | B_Lines |
|---|---|---|---|---|---|---|---|---|---|
| EXAMPLE 6A | | | | | | | | | |
| Parental Lines | | | | | | | | | |
| CMS lines 98OA-226 | 2.61 | 1.64 | 85.10 | 4.82 | 2.29 | 7.11 | 0.00 | 01GHYB8502 | 95YY501 |
| RF lines GA-I-097-26 | 3.54 | 2.13 | 86.18 | 2.39 | 2.17 | 4.56 | 0.03 | 01GHYB8502 | |
| F1 Hybrids | | | | | | | | | |
| 01GHyb8502 | 3.06 | 3.34 | 84.13 | 3.50 | 2.09 | 5.59 | 0.03 | | |
| F2 Harvested from F1 Hybrids | | | | | | | | | |
| 01GHYB8502 | | | 85.45* | 3.45 | 3.86 | 7.31 | | | |
| EXAMPLE 6B | | | | | | | | | |
| Parental Lines | | | | | | | | | |
| CMS lines 98OA-195 | 2.81 | 1.75 | 84.29 | 4.70 | 2.27 | 6.97 | 0.06 | 01GHYB8505 | 95YM501 |
| RF lines GA-I-096-93-03 | 3.77 | 2.97 | 83.76 | 3.25 | 1.64 | 4.89 | 0.04 | 01GHYB8505 | |
| F1 Hybrids | | | | | | | | | |
| 01GHyb8505 | 3.73 | 2.69 | 81.48 | 5.16 | 2.82 | 7.98 | 0.04 | | |
| F2 Harvested from F1 Hybrids | | | | | | | | | |
| 01GHYB8505 | | | 84.48* | 4.27 | 3.60 | 7.87 | | | |
| OTHER EXAMPLES | | | | | | | | | |
| Parental Lines | | | | | | | | | |
| CMS lines 98OA-252 | 2.51 | 1.50 | 84.96 | 4.61 | 2.95 | 7.56 | 0.00 | 01GHYB8503 | 95ZQ526 |
| 98OA-204 | 2.64 | 1.48 | 84.41 | 5.13 | 3.07 | 8.20 | 0.08 | 01GHYB8504 | 95YN503 |
| 98OA-174 | 2.72 | 1.61 | 84.13 | 5.11 | 2.66 | 7.77 | 0.03 | 01GHYB8506 | 95XE502 |
| RF lines GA-I-097-26 | 3.54 | 2.13 | 86.18 | 2.39 | 2.17 | 4.56 | 0.03 | 01GHYB8503 | |
| GA-I-096-93-02 | 3.77 | 2.97 | 83.76 | 3.25 | 1.64 | 4.89 | 0.04 | 01GHYB8504 | |
| GA-I-097-04-05 | 3.55 | 1.82 | 84.16 | 2.40 | 2.98 | 5.38 | 0.04 | 01GHYB8506 | |
| F1 Hybrids | | | | | | | | | |
| 01GHYB8503 | 2.95 | 3.25 | 83.71 | 3.78 | 2.16 | 5.94 | 0.04 | | |
| 01GHYB8504 | 3.89 | 2.56 | 81.12 | 5.57 | 2.61 | 8.18 | 0.03 | | |
| 01GHYB8506 | 3.17 | 2.84 | 84.28 | 3.68 | 2.06 | 5.74 | 0.03 | | |
| F2 Harvested from F1 Hybrids | | | | | | | | | |
| 01GHYB8503 | | | 84.46* | 6.13 | 1.53 | 7.66 | | | |
| 01GHYB8504 | | | 84.15* | 4.62 | 3.33 | 7.95 | | | |
| 01GHYB8506 | | | 83.97* | 5.16 | 3.84 | 9.00 | | | |

A "*" indicates that the fatty acid composition of this hybrid was determined by NIR. Fatty acid composition in all other samples was determined by GC.

Example 7

Production of Hybrid Canola with an Oleic Acid Content of 80% to 89% with Linolenic Acid Content of Less Than 4% in Plants Having Fad2 and Fad3 Co-Suppression An increase of oleic acid and decrease in linolenic acid composition in *Brassica* seed oil can be accomplished by inhibiting fad2 and fad3 desaturase gene expression. See U.S. Pat. No. 6,441,278. Plant cells can be transformed by the *Agrobacterium*-mediated transformation method with plasmids containing the coding sequence for the fad2 gene regulated by a seed-specific protein storage promoter (e.g., from napin, oleosin, or cruciferin). Regenerated plants from the transformed cells can be selected for increased oleic acid in the seed from co-suppression of the endogenous fad2 genes expression. Under regulation of the napin promoter, the fad2 sequence can result in co-suppression in the seeds to produce an oleic acid content of 84.1%, a linoleic acid content of 5.2%, and a linolenic acid content of 2.9%.

Fad3 expression can be reduced using the coding sequence for the fad3 gene regulated by similar seed specific promoters. The fatty acid content of seed oil for individual napin: Fad2 and napin: Fad3 constructs are shown in Table 7. Co-suppression with the fad3 sequence under the napin promoter produced a seed oil having an oleic acid content of 68.5%, a linoleic acid content of 22.1%, and a linolenic acid content of 1.2%

TABLE 7

Fatty Acid Profiles in Oil From Co-suppression in Canola Seeds

| Transgene Construct | 16:0 | 8:0 | 18:1 | 18:2 | 18:3 | 20:0 | 20:1 | 22:0 | 24:0 |
|---|---|---|---|---|---|---|---|---|---|
| Napin:Fad2 Co-suppression | 4.3 | 1.4 | 84.1 | 5.2 | 2.9 | 0.6 | 0.9 | 0.5 | 0.2 |
| Napin:Fad3 Co-suppression | 4.8 | 1.5 | 68.5 | 22.1 | 1.2 | 0.6 | 1.1 | 0.4 | 0.1 |

Crosses were made between the napin: Fad3 co-suppressed line designated 663-40 and the cruciferin: Fad2 co-suppressed line designated 691-215. Selfed progeny were advanced and selected for homozygous individuals of the recombinant constructs. The fatty acid profiles of the parent lines and the homozygous line having both of the constructs are shown in Table 8. The seed oil from plants having the combined co-suppression constructs had an oleic acid content of 86.2%, a linoleic acid content of 5.2%, and a linolenic acid content of 1.5%.

TABLE 8

Fatty Acid Profile of Homozygous Lines Exhibiting Fad2 and Fad3 Co-suppression

| Lines Number | Construct | 16:0 | 18:0 | 18:1 | 18:2 | 18:3 |
|---|---|---|---|---|---|---|
| 663-40 | Napin:Fad3 | 3.9 | 1.4 | 71.2 | 20.1 | 1.2 |
| 692-105-11 | Oleosin:Fad2 | 3.4 | 1.3 | 86.2 | 2.7 | 4.2 |
| 663-40 X 692-105-11 | Napin:Fad3 & Oleosin:Fad2 | 3.4 | 1.4 | 86.8 | 4.6 | 1.4 |

$F_1$ hybrids are made using female parents containing Ogura CMS and having the fad2 and fad 3 co-suppressed in the seed to confer the high oleic and low linolenic phenotype. The female is maintained by a B-line having same recombinant events for fad2 and fad3 co-suppression but without the Ogura CMS. The male or pollen parent contains a Kosena or Ogura fertility restorer gene and the same recombinant events for fad2 and fad 3 co-suppression in the seed as in the female to confer the high oleic and low linolenic phenotype. The fatty acid content of $F_1$ hybrid seed is about 86.8% oleic acid, about 4.6% linoleic acid, and about 1.4% linolenic acid. The fatty acid content of resulting $F_2$ seed from the $F_1$ hybrid is similar in fatty acid composition to the $F_1$ hybrid seed.

Example 8

Production of Hybrid Canola with an Oleic Acid Content of 80% to 89% with Linolenic Acid Content of Less Than 4% in Plants Having a Fad2 Mutation and a Fad3 Co-Suppression Event A cross was made between Q4275 and the napin: Fad3 co-suppressed line 663-40 to combine the mutations in the Fad2 genes and the recombinant construct for Fad3 co-suppression. After selfing and selection to reach homozygosity, the resulting plants had the high oleic and low linolenic acid phenotype of the parents (Table 9).

TABLE 9

Range of fatty acid profile for Fad3 co-suppression and Fad2 mutated lines tested in the field

| Lines Number | Range of expression | Fatty Acid Profile of Homozygous Lines with the Fad2 mutations and Fad3 Co-suppression | | | | |
|---|---|---|---|---|---|---|
| | | 16:0 | 18:0 | 18:1 | 18:2 | 18:3 |
| 663-40 | Min | 3.5 | 2.3 | 73.5 | 16.3 | 0.8 |
| | Max | 4.7 | 2.2 | 64.0 | 24.2 | 1.5 |
| Q4275 | Min | 3.2 | 3.3 | 85.0 | 1.8 | 2.0 |
| | Max | 3.0 | 2.3 | 86.6 | 1.7 | 2.6 |
| 663-40 X Q4275 | Min | 3.2 | 2.0 | 85.1 | 5.3 | 0.9 |
| | Max | 3.2 | 2.9 | 84.0 | 6.0 | 1.5 |

$F_1$ hybrids are made from female parents containing Ogura CMS and having the Q4275 fad2 mutations and fad3 co-suppressed in the seed to confer the high oleic and low linolenic phenotype. The female is maintained by a B-line having the same fad2 mutations and recombinant fad3 co-suppression event but without the Ogura CMS. The male or pollen parents contain a Kosena or Ogura fertility restorer gene and the same fad2 mutation and recombinant fad 3 co-suppression event in the seed as in the female to confer the high oleic and low linolenic phenotype. The fatty acid content of $F_1$ hybrid seed is 84 to 87% oleic acid, 4.6 to 6.0% linoleic acid, and 0.8 to 2.6% linolenic acid. The resulting $F_2$ seed from the $F_1$ hybrid would have a similar fatty acid composition.

Example 9

Characterization of TAG Structure of Oils from Hybrid and Non-Hybrid *Brassica* Plants The TAG composition and structure was determined for oil obtained from three non-hybrid *Brassica* varieties that produce CV65, CV75, or CV85 Clear Valley® oils (Cargill, Inc.), 50/50 blends of the CV65, CV75, and CV85 oils, and *Brassica* hybrids. A description of the lines is shown in Table 10. The fatty acid content of the parent lines used to produce the hybrids is shown in Table 11.

TABLE 10

Pedigree of Lines

| Seed Line | Oil Type | Type | Cross Combination | Pedigree (F × M) |
|---|---|---|---|---|
| IMC 109 | CV65 | Variety | NA | NA |
| IMC 208 | CV75 | Variety | NA | NA |
| IMC 304 | CV85 | Variety | NA | NA |
| CV65-CV75 | Low oleic blend | Blend | NA | NA |
| CV75-CV85 | High oleic blend | Blend | NA | NA |
| CV65-CV85 | Mid-oleic blend | Blend | NA | NA |
| 03H252 | Mid oleic | Hybrid | CV75 × CV75 | 00OA329R × 01PR10.011D |
| 03H259 | Mid oleic | Hybrid | CV65 × CV75 | 98OA290R × 01PR10.011D |
| 03H546 | Mid oleic | Hybrid | CV65 × CV85 | 00OA341R × 01PR20-31B |
| 03H628 | Mid oleic | Hybrid | CV85 × CV65 | 00OA41 × 01PR06RR.103A |
| 03H279 | High Oleic | Hybrid | CV85 × CV85 | 00OA237R × 01PR25-44A |
| 03H292 | High Oleic | Hybrid | CV85 × CV85 | 00OA309R × 01PR25-44A |
| 03H590 | High Oleic | Hybrid | CV85 × CV85 | 00OA237R × 01PR20-31B |

NA = not applicable

TABLE 11

Fatty acid composition of parent lines for hybrids.

| | C16:0 | C18:0 | C18:1 | C18:2 | C18:3 | C22:1 |
|---|---|---|---|---|---|---|
| Female | | | | | | |
| 00OA329 | 2.91 | 1.83 | 79.03 | 8.80 | 3.59 | 0.05 |
| 00OA341 | 3.30 | 1.76 | 64.85 | 23.25 | 3.22 | 0.04 |
| 00OA41 | 3.61 | 2.26 | 83.88 | 4.95 | 1.62 | 0.03 |
| 98OA290R | 3.70 | 1.86 | 64.09 | 22.89 | 2.43 | 0.07 |
| 00OA309R | 3.77 | 1.96 | 84.30 | 4.67 | 2.01 | 0.04 |
| 00OA237R | 3.70 | 2.49 | 85.24 | 2.07 | 2.62 | 0.03 |
| Male | | | | | | |
| 01PR10.011D | 3.41 | 1.33 | 78.22 | 10.54 | 2.92. | 0.04 |
| 01PR20-31B | 3.02 | 1.11 | 85.55 | 4.31 | 3.16 | 0.02 |
| 01PR06RR.103A | 4.33 | 1.82 | 65.45 | 22.11 | 2.58 | 0.03 |
| 01PR10.011D | 3.41 | 1.33 | 78.22 | 10.54 | 2.92 | 0.02 |
| 01PR25-44A | 3.24 | 1.49 | 83.34 | 4.21 | 4.24 | 0.04 |
| 01PR20-31B | 3.02 | 1.11 | 85.55 | 4.31 | 3.16 | 0.02 |

Oil samples were prepared from the varieties (V), blends (B), and hybrids (H) by hexane extracting seed (28 or 56 g) with a Soxhlet extractor. The hexane was removed from the oil with medium heat and nitrogen purging. Table 12 presents the fatty acid composition of each sample on an area percent basis. The oleic acid content for the CV65, CV75 and CV85 oils was 66.79%, 78.78%, and 79.87%, respectively. The oleic acid content of the 50/50 blends was 72.81%, 80.81%, and 73.99%. The oleic acid content for the CV75-CV85 blend was similar to the 85 hybrids. The CV75 hybrids ranged from 71.8% to 79.8% oleic acid with a CV75×CV75 line having the highest oleic acid (79.81%) content and lowest linoleic acid content (8.52%). The oleic acid content of the CV85 hybrids ranged from 81.62% to 82.41%.

TABLE 12

Fatty acid composition of oils.

| Sample | Oil Type | C16:0 | C18:0 | C18:1 | C18:2 | C18:3 |
|---|---|---|---|---|---|---|
| IMC109 | CV65 | 3.90 | 1.88 | 66.79 | 21.85 | 2.13 |
| IMC208 | CV75 | 3.57[1] | 2.17[2] | 78.78[3] | 9.29[4] | 2.45[5] |
| IMC304 | CV85 | 3.48 | 2.12 | 79.87 | 8.22 | 2.47 |
| CV65-CV75 | Low oleic blend | 3.74 | 2.02 | 72.81 | 15.61 | 2.28 |
| CV75-CV85 | High-oleic blend | 3.44 | 2.07 | 80.81 | 7.37 | 2.50 |
| CV65-CV85 | Mid oleic blend | 3.63 | 1.95 | 73.99 | 14.54 | 2.31 |
| 03H252 | CV75 H | 3.22 | 2.10 | 79.81 | 8.52 | 2.91 |
| 03H259 | CV75 H | 3.67 | 1.84 | 71.80 | 15.60 | 2.63 |
| 03H546 | CV75 H | 3.25 | 2.16 | 76.79 | 12.05 | 2.40 |
| 03H628 | CV75 H | 3.45 | 1.97 | 77.89 | 12.49 | 2.09 |
| 03H279 | CV85 H | 3.39 | 2.06 | 81.62 | 6.37 | 3.20 |
| 03H292 | CV85 H | 3.25 | 2.01 | 82.41 | 6.49 | 2.30 |
| 03H590 | CV85 H | 3.33 | 2.17 | 81.76 | 6.56 | 2.54 |

[1] n = 3, sd = 0 and % rsd = 0;
[2] n = 3, sd = 0.006 and % rsd = 0.27;
[3] n = 3, sd = 0.04 and % rsd = 0.05;
[4] n = 3, sd = 0.01 and % rsd = 0.11;
[5] n = 3, sd = 0.01 and % rsd = 0.41

TAG composition was determined by RP LC coupled to an ELS detector. Two Adsorbosphere C18 stationary phase LC columns were used in series. The mobile phase was a gradient of acetonitrile and methylene chloride (70% ACN/30%

CH$_2$Cl$_2$ to 40% ACN/60% CH$_2$Cl$_2$ in 30 min at 0.7 mL/min). The columns was maintained at 10° C. The ELSD settings were 35° C., Gain=6, and Nitrogen=3.5 bar (50 psi). Samples were made up in CH$_2$Cl$_2$. Triundecanoin (C33 TAG) was used as the internal standard (IS), and Triolein (OOO) was used as the external standard. Quantitation was done log-log. R$^2$ was 0.9971 and the equation was y=1.56x−0.73.

Figure 2:
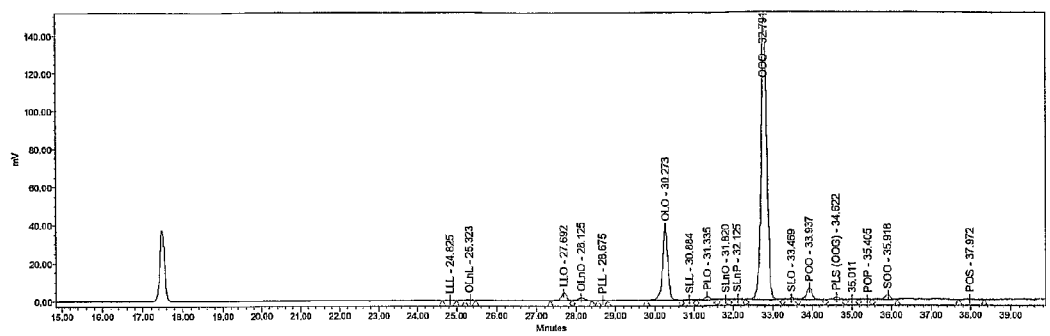
FIG. 2 is a chromatogram of the TAG profile of a 50/50 blend of CV75 and CV85 canola oil. The internal standard peak is at 17.5 min.
Figure 3:
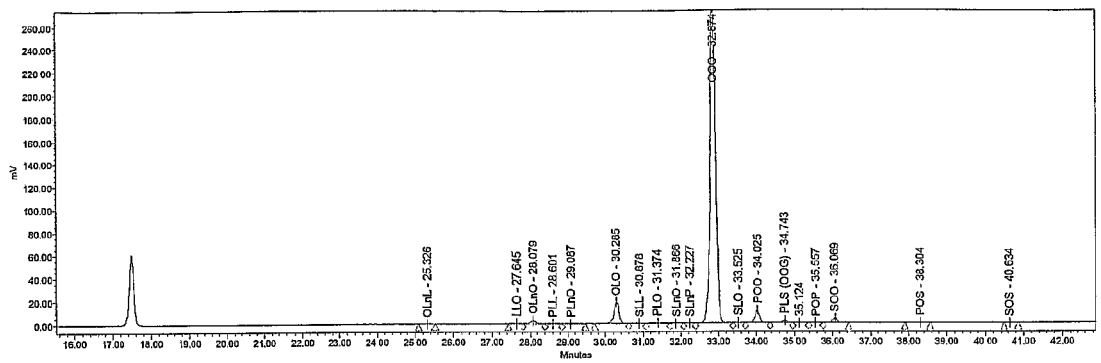
FIG. 3 is a chromatogram of the TAG profile of the 03H292 Brassica hybrid. The internal standard peak is at 17.5 min.

Table 13 shows the TAG composition for the varieties (V), blends (B) and hybrids (H) on an area percent basis. Values less than 0.2% were not recorded. The primary TAGs are LLO, OLO and OOO. In the varieties, as oleic acid increases so does OOO, while OLO and LLO decrease. The CV75× CV85 blend was similar to the 85 hybrids in composition, but the 85 hybrids were slightly lower in OLO and higher in OOO. Representative TAG profiles of the CV65 oil, the CV75/CV85 blend, and the 03H292 hybrid are shown in FIGS. 1-3, respectively.

TABLE 13

TAG composition of the canola oils.

| Seed Line | Oil Type | OLnL | LLO | OLnO | OLO | PLO | OOO | SLO | POO | PLS | SOO |
|---|---|---|---|---|---|---|---|---|---|---|---|
| IMC109 | CV65 | 0.26 | 5.57 | 0.58 | 37.92 | 1.39 | 50.16 | 0.44 | 2.32 | 0.27 | 0.45 |
| IMC208 | CV75 | ND | 0.25 | 0.88 | 10.23 | 0.34 | 83.25 | ND | 2.95 | 0.40 | 1.08 |
| IMC304 | CV85 | ND | ND | 0.79 | 6.07 | 0.29 | 85.20 | ND | 3.48 | 0.87 | 1.77 |
| CV65-CV75 | Low oleic blend | ND | 1.91 | 0.73 | 20.71 | 0.80 | 70.55 | 0.34 | 2.66 | 0.42 | 1.08 |
| CV75-CV85 | High-oleic blend | ND | 0.25 | 0.88 | 7.92 | 0.38 | 84.89 | 0.20 | 3.17 | 0.55 | 1.17 |
| CV65-CV85 | Mid oleic blend | ND | 1.69 | 0.74 | 17.99 | 0.83 | 73.28 | 0.32 | 2.79 | 0.48 | 1.07 |
| 03H252 | CV75 H | ND | 0.21 | 1.37 | 10.04 | 0.37 | 81.85 | 0.24 | 3.39 | 0.57 | 1.31 |
| 03H259 | CV75 H | 0.24 | 2.08 | 0.93 | 25.34 | 1.04 | 65.37 | 0.38 | 2.77 | 0.42 | 0.76 |
| 03H546 | CV75 H | ND | 0.72 | 0.95 | 16.15 | 0.50 | 76.90 | 0.32 | 2.61 | 0.43 | 0.98 |
| 03H628 | CV75 H | ND | 0.78 | 0.67 | 16.93 | 0.58 | 76.03 | 0.29 | 2.77 | 0.54 | 0.83 |
| 03H279 | CV85 H | ND | ND | 1.56 | 5.46 | 0.25 | 87.06 | ND | 3.21 | 0.53 | 1.15 |
| 03H292 | CV85 H | ND | ND | 0.89 | 5.60 | 0.29 | 87.78 | ND | 2.98 | 0.54 | 1.06 |
| 03H590 | CV85 H | ND | ND | 1.11 | 6.26 | 0.29 | 86.15 | ND | 3.50 | 0.61 | 1.31 |

ND = not detectable

Example 10

Production of Hybrid Canola with a C18:1 Content from 80% to 89% and C18:3 Content of Less than 4% Content in Plants Having a Fad3 Mutation and Two Fad2 Mutations Hybrid canola varieties yielding seeds having an oleic acid content of 80-89% and an α-linolenic acid content of less than 4% were produced using parents having the mutations from IMC02 that confer a low linolenic acid phenotype and both fad2 mutations from Q4275. Female parents contained Ogura CMS and the male parents contained an Ogura-type fertility restorer gene. The fatty acid content of seeds of the parent lines is shown in Table 14. In the tent for hybrid 04H033, 3 female rows were planted containing two different seed samples of line 00OA23 and 7 male restorer rows were planted from the same seed sample of line 03RF10.52. In the tent for hybrid 04H044, 3 female rows were planted from three different seed samples of line 00OA23 C and 7 male restorer rows were planted from the same seed sample of line 03RF09.37. In the tent for hybrid 04H046, 3 female rows were planted from the same seed sample of line 00OA43-1 C and 7 male restorer rows were planted from the same seed sample of line 03RF09.37. In the tent for hybrid 04H048, 3 female rows were planted from the same seed sample of line 00OA65-2 C and 7 male restorer rows were planted from the same seed sample of line 03RF09.37.

TABLE 14

Fatty Acid Content of Parental Lines

| Hybrid | Line | C14:0 | C16:0 | 16:1 | C18:0 | C18:1 | C18:2 | C18:3 |
|---|---|---|---|---|---|---|---|---|
| 04H033 (00OA23-1 × 03RF10.52) | | | | | | | | |
| Female | 00OA23 | 0.05 | 3.23 | 0.26 | 2.44 | 85.20 | 3.66 | 1.76 |
| Female | 00OA23-1 | 0.06 | 3.57 | 0.31 | 3.47 | 83.91 | 3.46 | 1.59 |
| Female | 00OA23-1 | 0.06 | 3.57 | 0.31 | 3.47 | 83.91 | 3.46 | 1.59 |
| Male | 03RF10.52 | 0.06 | 3.26 | 0.32 | 1.73 | 86.91 | 3.08 | 1.88 |

TABLE 14-continued

Fatty Acid Content of Parental Lines

04H044 (00OA23 × 03RF09.37)

| | | | | | | | | |
|---|---|---|---|---|---|---|---|---|
| Female | 00OA23 | 0.05 | 3.23 | 0.26 | 2.44 | 85.20 | 3.66 | 1.76 |
| Female | 00OA23-2 | 0.06 | 3.54 | 0.28 | 3.66 | 83.57 | 3.53 | 1.56 |
| Female | 00OA23-3 | 0.07 | 3.99 | 0.40 | 3.47 | 82.56 | 3.90 | 1.88 |
| Male | 03RF09.37 | 0.07 | 3.12 | 0.37 | 1.61 | 86.50 | 2.77 | 2.22 |

04H046 (00OA43-1 × 03RF09.37)

| | | | | | | | | |
|---|---|---|---|---|---|---|---|---|
| Female | 00OA43-1 | 0.04 | 3.35 | 0.31 | 3.30 | 84.84 | 3.07 | 1.43 |
| Male | 03RF09.37 | 0.07 | 3.12 | 0.37 | 1.61 | 86.50 | 2.77 | 2.22 |

04H048 (00OA65-2 × 03RF09.37)

| | | | | | | | | |
|---|---|---|---|---|---|---|---|---|
| Female | 00OA65-2 | 0.06 | 3.79 | 0.33 | 2.20 | 85.00 | 3.83 | 1.73 |
| Male | 03RF09.37 | 0.07 | 3.12 | 0.37 | 1.61 | 86.50 | 2.77 | 2.22 |

| Hybrid | C20:0 | C20:1 | C20:2 | C22:0 | C22:1 | C24:0 | C24:1 | FDA |
|---|---|---|---|---|---|---|---|---|
| 04H033 (00OA23-1 × 03RF10.52) | | | | | | | | |
| Female | 0.91 | 1.41 | 0.05 | 0.46 | 0.05 | 0.38 | 0.13 | 7.47 |
| Female | 1.15 | 1.27 | 0.04 | 0.51 | 0.04 | 0.49 | 0.14 | 9.25 |
| Female | 1.15 | 1.27 | 0.04 | 0.51 | 0.04 | 0.49 | 0.14 | 9.25 |
| Male | 0.62 | 1.42 | 0.04 | 0.33 | 0.02 | 0.25 | 0.08 | 6.25 |
| 04H044 (00OA23 × 03RF09.37) | | | | | | | | |
| Female | 0.91 | 1.41 | 0.05 | 0.46 | 0.05 | 0.38 | 0.13 | 7.47 |
| Female | 1.22 | 1.34 | 0.04 | 0.55 | 0.02 | 0.50 | 0.15 | 9.53 |
| Female | 1.17 | 1.28 | 0.04 | 0.55 | 0.03 | 0.51 | 0.16 | 9.76 |
| Male | 0.59 | 1.38 | 0.04 | 0.35 | 0.00 | 0.18 | 0.81 | 5.92 |
| 04H046 (00OA43-1 × 03RF09.37) | | | | | | | | |
| Female | 1.18 | 1.24 | 0.04 | 0.58 | 0.02 | 0.49 | 0.13 | 8.93 |
| Male | 0.59 | 1.38 | 0.04 | 0.35 | 0.00 | 0.18 | 0.81 | 5.92 |
| 04H048 (00OA65-2 × 03RF09.37) | | | | | | | | |
| Female | 0.81 | 1.29 | 0.05 | 0.42 | 0.03 | 0.34 | 0.13 | 7.62 |
| Male | 0.59 | 1.38 | 0.04 | 0.35 | 0.00 | 0.18 | 0.81 | 5.92 |

F1 hybrid seeds were harvested from the female plants and analyzed for fatty acid composition (Table 15). The F1 hybrid seeds had an C18:1 content that ranged from 84.82% to 86.12% and a C18:3 content that ranged from 2.3% to 3.18%. The F1 hybrid seeds were planted and F2 seeds were harvested from field plots of resulting plants. The fatty acid composition of the F2 seeds is shown in Table 16 (NIR analysis) and Table 17 (GC analysis). For F2 seed samples analyzed by NIR, the C18:1 content ranged from 83.51% to 84.46% and the C18:3 content ranged from 1.87% to 2.55%. By GC, the C18:1 content ranged from 83.69% to 84.38% and the C18:3 content ranged from 2.91% to 3.29%. The average daily temperature was 9.8° C. for the last three weeks before harvesting the seeds vs. an average temperature of 12.5° C. for this same period, based on historic data for the last 15 years.

TABLE 15

Fatty acid composition of F1 hybrid seed

| Hybrid | C18:1 | C18:2 | C18:3 | FDA | Oil | Chlorophyll | Glucosinolates | Moisture | Protein |
|---|---|---|---|---|---|---|---|---|---|
| 04H033 | 85.81 | 3.80 | 2.30 | 6.31 | 43.77 | 7.43 | 12.94 | 4.25 | 32.24 |
| 04H044 | 84.82 | 3.55 | 3.18 | 6.24 | 43.44 | 7.46 | 18.78 | 4.01 | 31.73 |
| O4H046 | 85.00 | 3.58 | 2.95 | 6.29 | 44.14 | 9.17 | 15.40 | 4.43 | 32.15 |
| 04H048 | 86.12 | 2.74 | 2.66 | 5.73 | 45.04 | 12.70 | 12.54 | 3.92 | 32.53 |

TABLE 16

Fatty acid composition of F2 hybrid seed as determined by NIR

| Hybrid | C18:1 | C18:2 | C18:3 | Chlorophyll | Glucosinolates | Moisture | Oil | Protein | Total Sat |
|---|---|---|---|---|---|---|---|---|---|
| 04H033 | 83.51 | 5.43 | 1.87 | 24.42 | 16.17 | 3.26 | 50.74 | 24.17 | 6.31 |
| 04H044 | 84.16 | 4.26 | 2.55 | 18.50 | 19.61 | 3.30 | 49.70 | 23.95 | 6.04 |
| O4H046 | 83.78 | 4.89 | 2.18 | 18.33 | 18.07 | 3.88 | 49.49 | 25.66 | 5.87 |
| 04H048 | 84.46 | 3.90 | 2.49 | 18.83 | 15.77 | 3.69 | 50.04 | 25.17 | 5.88 |

TABLE 17

| Hybrid | C14:0 | C16:0 | C16:1 | C18:0 | C18:1 | C18:2 | C18:3 | C20:0 | C20:1 | C20:2 | C22:0 | C22:1 | C24:0 | C24:1 | FDA |
|---|---|---|---|---|---|---|---|---|---|---|---|---|---|---|---|
| 04H033 | 0.04 | 2.93 | 0.22 | 1.75 | 84.29 | 4.83 | 2.91 | 0.67 | 1.52 | 0.04 | 0.38 | 0.04 | 0.19 | 0.19 | 5.96 |
| 04H044 | 0.04 | 2.90 | 0.23 | 1.92 | 83.79 | 4.65 | 3.29 | 0.74 | 1.54 | 0.04 | 0.42 | 0.03 | 0.22 | 0.20 | 6.23 |
| 04H046 | 0.03 | 2.80 | 0.23 | 1.88 | 84.38 | 4.29 | 3.03 | 0.76 | 1.63 | 0.04 | 0.44 | 0.04 | 0.23 | 0.22 | 6.14 |
| 04H048 | 0.04 | 2.97 | 0.23 | 1.86 | 83.69 | 4.74 | 3.31 | 0.73 | 1.54 | 0.04 | 0.42 | 0.03 | 0.19 | 0.22 | 6.21 |

Fatty acid composition of F2 hybrid seed as determined by GC

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A canola oil having an oleic acid content from about 71% to about 80% and an α-linolenic acid content from about 2.0% to about 4.2%, an OLO content from about 22% to about 36% and an OOO content from about 51% to about 69%, wherein OLO is a triacylglycerol comprising two oleic acids and one linoleic acid and OOO is triolein.

2. The canola oil of claim 1, wherein said oil has a LLO content from 2% to about 5%, wherein LLO is a triacylglycerol comprising two linoleic acids and one oleic acid.

3. The canola oil of claim 1, wherein said oleic acid content is from about 71.5% to about 78%.

4. The canola oil of claim 1, wherein said α-linolenic acid content is from about 2.1% to about 2.9%.

5. The canola oil of claim 1, wherein said OLO content is from about 23% to about 27%.

6. The canola oil of claim 1, wherein said OOO content is from about 60% to about 68%.

7. The canola oil of claim 2, wherein said LLO content is 2.1%.

8. A canola oil having an oleic acid content from about 71% to about 80% and an α-linolenic acid content from about 1.5% to about 4.5%, an OLO content from about 11% to about 17% and an OOO content from about 74% to about 82%, wherein OLO is a triacylglycerol comprising two oleic acids and one linoleic acid and OOO is triolein.

9. The canola oil of claim 8, wherein said oil has an LLO content from about 0.4% to about 1.5%, wherein LLO is a triacylglycerol comprising two linoleic acids and one oleic acid.

10. The canola oil of claim 8, wherein said oleic acid content is about 73% to about 78%.

11. The canola oil of claim 8, wherein said α-linolenic acid content is about 2.1% to about 2.9%.

12. The canola oil of claim 8, wherein said OLO content is about 14% to about 17%.

13. The canola oil of claim 8, wherein said OOO content is about 75% to about 80%.

14. The canola oil of claim 9, wherein said LLO content is 0.7% to 0.8%.

15. A food composition comprising the canola oil of claim 1 or 8.

16. The food composition of claim 15, wherein said food composition is a bakery product, a breakfast bar, a breakfast cereal, a cracker, or a fried food.

17. The food composition of claim 15, wherein said food composition is a cookie, muffin, pie filling, pastry, pie crust, doughnut, bread, or cake.

18. The food composition of claim 16, wherein said fried food is a snack chip or a French fry.

19. The food composition of claim 15, wherein said food composition is a corn chip or potato chip.

20. A spray coating comprising the canola oil of claim 1 or 8.

21. The spray coating of claim 20, said spray coating further comprising another vegetable oil, an antioxidant, or a seasoning.

22. The spray coating of claim 20, wherein said spray coating further comprises cottonseed oil, soybean oil, corn oil, or sunflower oil.

23. The canola oil of claim 1, wherein said OLO is an oleic acid/linoleic acid/oleic acid triacylglycerol in which the acid moieties are.

24. The canola oil of claim 2, wherein said LLO is a linoleic acid/linoleic acid/oleic acid triacylglycerol.

25. The canola oil of claim 8, wherein said OLO is an oleic acid/linoleic acid/oleic acid triacylglycerol.

26. The canola oil of claim 9, wherein said LLO is a linoleic acid/linoleic acid/oleic acid triacylglycerol.

* * * * *

UNITED STATES PATENT AND TRADEMARK OFFICE
CERTIFICATE OF CORRECTION

PATENT NO.       : 8,080,680 B2                                  Page 1 of 1
APPLICATION NO.  : 11/575477
DATED            : December 20, 2011
INVENTOR(S)      : Lorin R. Debonte et al.

It is certified that error appears in the above-identified patent and that said Letters Patent is hereby corrected as shown below:

In column 11, lines 29-30, delete "Tetrahyinena" and insert -- Tetrahymena --, therefor.

In column 19, line 11, delete "all" and insert -- an --, therefor.

In column 28, line 48, delete "00HA0104" and insert -- 02HA0104 --, therefor.

In column 28, line 60, delete "00HA0107," and insert -- 02HA0107, --, therefor.

In column 42, lines 41-42, delete "in which the acid moieties are".

Signed and Sealed this
Twentieth Day of March, 2012

David J. Kappos
*Director of the United States Patent and Trademark Office*